United States Patent [19]
Nissing et al.

[11] Patent Number: 6,133,166
[45] Date of Patent: *Oct. 17, 2000

[54] CLEANING ARTICLES COMPRISING A CELLULOSIC FIBROUS STRUCTURE HAVING DISCRETE BASIS WEIGHT REGIONS TREATED WITH A HIGH INTERNAL PHASE INVERSE EMULSION

[75] Inventors: Nicholas James Nissing, Cincinnati; Steven Lee Barnholtz, Hamilton; David William Cabell, Cincinnati, all of Ohio

[73] Assignee: The Procter & Gamble Company, Cincinnati, Ohio

[*] Notice: This patent is subject to a terminal disclaimer.

[21] Appl. No.: 08/886,764

[22] Filed: Jul. 1, 1997

[51] Int. Cl.$^7$ .............................. A01N 25/34; B32B 9/06
[52] U.S. Cl. ......................... 442/61; 424/402; 428/484; 428/486; 428/537.5
[58] Field of Search .............................. 442/61; 428/486, 428/484, 537.5; 424/402

[56] References Cited

U.S. PATENT DOCUMENTS

| | | | |
|---|---|---|---|
| 2,868,824 | 1/1959 | Haluska | 556/444 |
| 3,215,707 | 11/1965 | Rense | 548/546 |
| 3,231,587 | 1/1966 | Rense | 549/255 |
| 3,818,533 | 6/1974 | Scheuer | 15/104.93 |
| 3,819,530 | 6/1974 | Ratledge et al. | 516/38 |
| 3,847,637 | 11/1974 | Luszczak | 106/271 |
| 3,896,807 | 7/1975 | Buchalter | 604/289 |
| 3,919,149 | 11/1975 | Cushman et al. | 524/111 |
| 3,965,518 | 6/1976 | Muoio | 15/104.93 |
| 3,982,993 | 9/1976 | Fife | 162/158 |
| 4,043,829 | 8/1977 | Ratledge et al. | 106/271 |
| 4,082,887 | 4/1978 | Coates | 442/114 |
| 4,104,403 | 8/1978 | Barker et al. | 514/784 |
| 4,112,167 | 9/1978 | Dake et al. | 428/154 |
| 4,117,199 | 9/1978 | Gotoh et al. | 428/486 |
| 4,122,029 | 10/1978 | Gee et al. | 516/23 |
| 4,137,358 | 1/1979 | Hartz | 442/149 |
| 4,203,877 | 5/1980 | Baker | 524/500 |
| 4,246,423 | 1/1981 | Martin | 556/423 |
| 4,293,611 | 10/1981 | Martin | 442/80 |
| 4,339,276 | 7/1982 | Yokoyama et al. | 106/271 |
| 4,377,649 | 3/1983 | Sweeney et al. | 524/49 |
| 4,381,241 | 4/1983 | Romenesko et al. | 504/127 |
| 4,385,049 | 5/1983 | Cuca | 514/786 |
| 4,446,051 | 5/1984 | Berthod et al. | 516/23 |
| 4,468,254 | 8/1984 | Yokoyama et al. | 106/271 |
| 4,481,243 | 11/1984 | Allen | 428/154 |
| 4,513,051 | 4/1985 | Lavash | 428/212 |
| 4,514,345 | 4/1985 | Johnson et al. | 264/425 |
| 4,520,160 | 5/1985 | Brown | 524/765 |
| 4,606,913 | 8/1986 | Aronson et al. | 424/59 |
| 4,698,178 | 10/1987 | Hüttinger et al. | 516/23 |

(List continued on next page.)

FOREIGN PATENT DOCUMENTS

| | | | |
|---|---|---|---|
| 1 132 908 | 10/1982 | Canada | 167/310 |
| 0 110 678 A2 | 6/1984 | European Pat. Off. | C08K 7/00 |
| 0 365 160 B1 | 4/1990 | European Pat. Off. | A61K 7/40 |
| 0 501 791 A3 | 9/1992 | European Pat. Off. | C08G 77/46 |
| 0 545 002 A1 | 6/1993 | European Pat. Off. | C08G 77/46 |
| 0 631 774 A1 | 1/1995 | European Pat. Off. | A61K 9/113 |
| 0 259 034 A2 | 3/1998 | European Pat. Off. | A61K 7/00 |
| 2 321 389 | 12/1976 | France | B32B 29/02 |
| 3341770 A1 | 5/1983 | Germany | A61K 9/06 |
| 155758 | 9/1981 | India | A61K 7/00 |
| 2/152920 | 6/1990 | Japan | A61K 7/50 |
| 3/168118 | 7/1991 | Japan | A47L 13/17 |
| 05070337 | 3/1993 | Japan | A61K 7/48 |
| 5-9144426 | 8/1994 | Japan . | |
| 1059541 | 2/1967 | United Kingdom . | |
| 2055689 | 3/1981 | United Kingdom | B32B 3/30 |
| 2 113 236 | 8/1983 | United Kingdom | C08L 83/12 |
| WO 87/03613 | 6/1987 | WIPO | C10M 173/00 |
| WO 94/02120 | 2/1994 | WIPO | A61K 9/113 |
| WO 95/16824 | 6/1995 | WIPO | D21H 17/14 |
| WO 96/14835 | 5/1996 | WIPO | A61K 9/70 |
| WO 96/34035 | 10/1996 | WIPO . | |

OTHER PUBLICATIONS

"Dow Corning Q2–5200 Formulation Aid", Dow Corning Corporation (1990).

Primary Examiner—Terrel Morris
Assistant Examiner—John J. Guarriello
Attorney, Agent, or Firm—Donald E. Hasse; Caroline Wei-Berk; Carl J. Roof

[57] ABSTRACT

Disclosed are articles useful in cleansing, and particularly wet-like cleansing wipes, which are dry until used, where fluid is released from the article. These articles comprise:

a. a carrier comprising a cellulosic fibrous structure having at least a first region of relatively high basis weight that comprises an essentially continuous network and a second region of a plurality of mutually discrete regions of relatively low basis weight which are circumscribed by the high basis weight first region; and b. an emulsion applied to the carrier, where the emulsion provides fluid for cleaning when shear forces are applied to the article.

The first and second regions of the cellulosic fibrous structure are disposed in a nonrandom, repeating pattern. The articles offer a number of significant advantages over prior cleaning products when in the form of wet-like cleansing wipes such as those used for cleaning of hardsurfaces (e.g., floors, countertops, sinks, bathtubs, toilets, and the like). The inclusion of low basis weight regions avoids substantial fluid retention by the cellulosic fibrous substrate, which allows fluid delivery to the surface being cleaned.

The articles can be used in many applications requiring the delivery of polar materials, in particular water and water-soluble or dispersible actives. These include toilet tissue, wipes for personal cleansing, such as baby wipes, as well as those for the delivery of water-soluble or dispersible anti-microbials or pharmaceutical actives.

45 Claims, 3 Drawing Sheets

U.S. PATENT DOCUMENTS

| | | | |
|---|---|---|---|
| 4,708,753 | 11/1987 | Forsberg | 149/2 |
| 4,782,095 | 11/1988 | Gum | 514/937 |
| 4,801,447 | 1/1989 | Gum | 424/68 |
| 4,844,756 | 7/1989 | Forsberg | 149/2 |
| 4,853,474 | 8/1989 | Bahr et al. | 556/445 |
| 4,875,927 | 10/1989 | Tadros | 504/235 |
| 5,021,405 | 6/1991 | Klimisch | 514/63 |
| 5,047,175 | 9/1991 | Forsberg | 516/22 |
| 5,073,235 | 12/1991 | Trokhan | 162/199 |
| 5,133,972 | 7/1992 | Ferrini et al. | 424/449 |
| 5,136,068 | 8/1992 | Bahr et al. | 516/20 |
| 5,162,378 | 11/1992 | Guthauser | 514/785 |
| 5,210,102 | 5/1993 | Klimisch | 514/784 |
| 5,245,025 | 9/1993 | Trokhan et al. | 536/56 |
| 5,247,044 | 9/1993 | Crivello et al. | 528/15 |
| 5,277,761 | 1/1994 | Van Phan et al. | 162/109 |
| 5,292,503 | 3/1994 | Raleigh et al. | 424/59 |
| 5,362,482 | 11/1994 | Yoneyama et al. | 424/69 |
| 5,378,455 | 1/1995 | Kealey et al. | 424/73 |
| 5,387,417 | 2/1995 | Rentsch | 424/401 |
| 5,470,551 | 11/1995 | Dubief et al. | 424/70.12 |
| 5,482,703 | 1/1996 | Pings | 424/70.12 |
| 5,503,715 | 4/1996 | Trokhan et al. | 162/296 |
| 5,525,345 | 6/1996 | Warner et al. | 424/402 |
| 5,534,326 | 7/1996 | Trokhan et al. | 428/131 |
| 5,756,112 | 5/1998 | Mackey | 424/402 |

CLEANING ARTICLES COMPRISING A CELLULOSIC FIBROUS STRUCTURE HAVING DISCRETE BASIS WEIGHT REGIONS TREATED WITH A HIGH INTERNAL PHASE INVERSE EMULSION

FIELD OF THE INVENTION

This application relates to wet-like cleaning wipes that comprise a carrier treated with a high internal phase inverse emulsion comprising a continuous lipid external phase and a polar internal phase. The carrier is in the form of a cellulosic fibrous structure having plural regions discriminated by basis weights. More particularly, the cellulosic fibrous structure has an essentially continuous high basis weight region and discrete low basis weight regions. The wipes are useful in various applications, including those for hard surface cleaning and personal cleansing such as baby wipes, and for removal of perianal soils such as toilet tissue.

BACKGROUND OF THE INVENTION

Nonwoven webs or sheets such as those made of paper find extensive use in modern society in the context of household cleaning activity. Paper towels, for example, are a staple item of commerce which have long been used to wipe up liquid spills and to remove stains and/or soil from hard surfaces such as window glass, countertops, sinks, porcelain and metal fixtures, walls and the like, and from other surfaces such as carpeting or furniture.

Paper towels products which are especially useful for household cleaning have attributes which include relatively low density, high bulk, acceptable softness, high absorbency for both aqueous and nonaqueous liquids and acceptable strength and integrity, especially when wet. Prior art towel products having such attributes, and processes for their preparation, have been disclosed, for example, in Ayers, U.S. Pat. No. 3,905,863, issued Sep. 16, 1975; Ayers, U.S. Pat. No. 3,974,025, issued Aug. 10, 1976; Trokhan, U.S. Pat. No. 4,191,609, issued Mar. 4, 1980; Wells and Hensler, U.S. Pat. No. 4,440,597, issued Apr. 3, 1984; Trokhan, U.S. Pat. No. 4,529,840, issued Jul. 16, 1985; and Trokhan, U.S. Pat. No. 4,637,859, issued Jan. 20, 1987. Paper towels, such as those of the types described in the foregoing patents, are especially useful for absorbing and wiping up liquid spills from both hard surfaces and other surfaces such as furniture and carpets. Paper towel products, however, are also frequently used in combination with liquid cleaning solutions or solvents, to remove soil or stains from surfaces to which such soil or stains may be especially securely affixed. Such soil or stains, for example, may include food material on stove, oven, or cooking utensil surfaces, soap scum found in bathtubs and sinks, food and beverage stains on kitchen counters, ink or crayon markings on walls and furniture, and the like. These prior art materials typically require the consumer to clean soils and stains using a separate cleaning solution and wiping article, which involves a level of inconvenience.

To address this issue of convenience, pre-wetted wiping articles have been developed, particularly in the area of baby wipes. These pre-wetted wipes are typically kept in a dispenser and are typically soaked in a reservoir of a moistening solution. There is often a lack of consistency in terms of the moisture content of each of the wipes, and the wipes feel cold to the touch. Also, because the main purpose of such wipes is to clean, these wipes generally exhibit relatively poor post-cleaning absorbency.

Co-pending U.S. patent application Ser. No. 08/336,456 (hereafter "'456 application"), filed Nov. 9, 1994 by L. Mackey et al., and co-pending U.S. patent application Ser. No. 08/761,097, filed Dec. 5, 1996 by L. Mackey et al. (hereafter "'097 application") disclose and claim wet-like cleansing wipes that are especially useful in removing perianal soils. These cleansing wipes comprise a substrate material (e.g., a nonwoven) that is treated with a water-in-lipid emulsion. These wipes have a number of significant advantages over prior cleaning products, especially when in the form of wet-like cleansing wipes used to remove perianal soils. These articles release significant quantities of water during use for comfortable, more effective cleaning. The continuous lipid phase of the emulsion is sufficiently brittle so as to be easily disrupted by low shear contact (e.g., during the wiping of the skin) to readily release this internal water phase, but sufficiently tough at elevated temperatures where the lipid is melted to avoid premature release of the water phase during the rigors of processing. The continuous lipid phase of these articles is also sufficiently stable during storage so as to prevent significant evaporation of the internal water phase. The normal tensile strength and flushability properties of these articles are not adversely affected when treated with the high internal phase inverse emulsions of the present invention. As a result, users of these articles get comfortable, efficient, moist cleaning without having to change their normal cleaning habits. The application also indicates that the technology is readily useful with other wipes, including wipes for cleaning hard surfaces.

In spite of the significant improvements over prior cleansing wipes, the substrates (also referred to as "carriers") specifically described in the '456 application are generally highly absorbent materials that, upon shearing of the emulsion in use, retain a significant amount of fluid in the carrier. As a result, at least for certain end-uses (e.g., hard surface wipes), suboptimal fluid levels are delivered to the surface to be cleaned. As such, it is necessary to treat the substrate with additional amounts of emulsion to account for the level of fluid retained by the carrier.

Accordingly, in certain circumstances, it would be desirable to provide products for cleaning that offer the benefits provided by the cleansing wipes described in the co-pending '456 and '097 applications, but which require treatment with reduced levels of emulsion. In this regard, a carrier that retains a relatively small amount of fluid upon emulsion rupture, but which absorbs the fluid after the wiping process, is highly desirable.

Accordingly, it is an object of the present invention to provide cellulose-based wiping articles which (i) are initially dry to the touch, but are capable of delivering fluid during the wiping process, (ii) allow transfer of fluid released from the emulsion of the article to the item being cleaned, and (iii) have desirably high overall absorbent capacity for liquids and especially effective soil and stain removal performance.

SUMMARY OF THE INVENTION

The present invention relates to articles useful in cleansing, and particularly wet-like cleansing wipes. These articles comprise:

a. a carrier comprising a cellulosic fibrous structure having at least a first region of relatively high basis weight that comprises an essentially continuous network and a second region of a plurality of mutually discrete regions of relatively low basis weight which are circumscribed by the high basis weight first region; and b. an emulsion applied to the carrier, the emulsion comprising:

(1) from about 2 to about 60% of a continuous, solidified external lipid phase comprising a waxy lipid material having a melting point of about 30° C. or higher;

(2) from about 39 to about 97% of an internal polar phase dispersed in the external lipid phase; and (3) an effective amount of an emulsifier capable of forming the emulsion when the external lipid phase is in a fluid state.

The first and second regions of the cellulosic fibrous structure are disposed in a nonrandom, repeating pattern. The articles of the present invention offer a number of significant advantages over prior cleaning products when in the form of wet-like cleansing wipes such as those used for cleaning of hardsurfaces (e.g., floors, countertops, sinks, bathtubs, toilets, and the like). Applicants have discovered that an important aspect of cleaning performance is the avoidance of substantial fluid retention by the cellulosic fibrous substrate.

The articles of the present invention can be used in many applications requiring the delivery of polar materials, in particular water and water-soluble or dispersible actives. These include wipes for personal cleansing, such as baby wipes, as well as those for the delivery of water-soluble or dispersible antimicrobials or pharmaceutical actives.

These articles can also perform multiple functions. For example, the high internal phase inverse emulsion applied to these articles can be formulated to provide cleaning and waxing benefits at the same time when used on items such as furniture, shoes, automobiles, and the like.

BRIEF DESCRIPTION OF THE DRAWINGS

While the specification concludes with claims particularly pointing out and distinctly claiming the present invention, it is believed the same will be better understood by the following specification taken in conjunction with the associated drawings in which like components are given the same reference numeral and:

DETAILED DESCRIPTION OF THE INVENTION

I. Definitions

Figure 1:
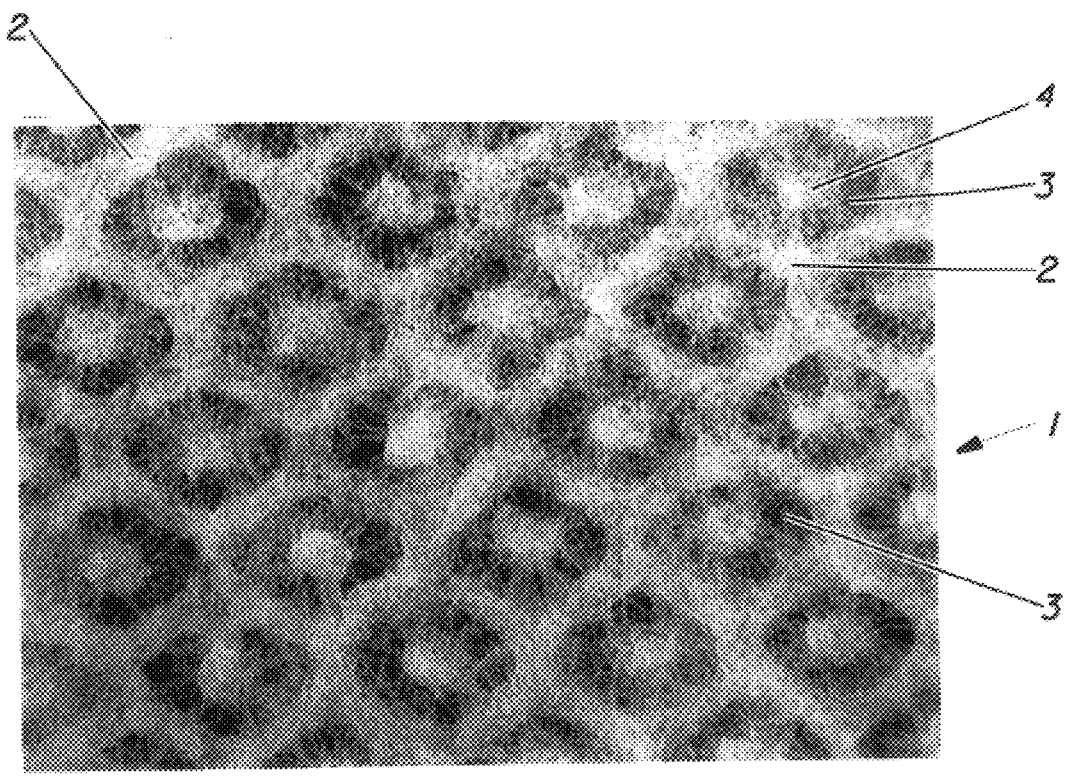
FIG. 1 is a top plan photomicrographic view (10× magnification) of a cellulosic fibrous structure useful in the present invention having discrete regions.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the terms "detergent", "detersive surfactant" and "detergent surfactant" are used interchangeably, and refer to any substance that reduces the surface tension of water, specifically a surface-active agent which concentrates at oil-water interfaces, exerts emulsifying action, and thus aids in removing soils.

As used herein, the term "hydrophilic" is used to refer to surfaces that are wettable by aqueous fluids deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a fluid (i.e., hydrophilic) when either the contact angle between the fluid and the surface is less than 90°, or when the fluid tends to spread spontaneously across the surface, both conditions normally co-existing. Conversely, a surface is considered to be "hydrophobic" if the contact angle is greater than 90° and the fluid does not spread spontaneously across the surface.

As used herein, the term "polar" means a molecule that possesses a dipole moment, i.e., a molecule of which the positive and negative electrical charges are permanently separated, as opposed to a nonpolar molecule in which the charges coincide. A "polar fluid" may comprise one or more polar constituents.

As used herein, the term "polarphilic" is used to refer to surfaces that are wettable by polar fluids deposited thereon. Polarphilicity and wettability are typically defined in terms of contact angle and the surface tension of the fluids and solid surfaces involved. A surface is said to be wetted by a polar fluid (i.e., polarphilic) when either the contact angle between the polar fluid and the surface is less than 90°, or when the polar fluid tends to spread spontaneously across the surface, both conditions normally co-existing. Conversely, a surface is considered to be "polarphobic" if the contact angle is greater than 90° and the fluid does not spread spontaneously across the surface. Since water is generally the preferred polar material used in the present invention, preferred embodiments discussed herein refer to a substrate's "hydrophilicity" and "hydrophobicity". However, use of such terms is not so limited and should be read to include "polarphilic" and "polarphobic" substrates.

All percentages, ratios and proportions used herein are by weight unless otherwise specified.

II. Articles

A. Cellulosic Fibrous Structure

To meet the needs of the consumer, the cellulosic fibrous structures useful herein must balance several competing interests. For example, cellulosic fibrous structure must deliver sufficient levels of fluid released from the emulsion to provide adequate cleaning performance. In this regard, the cellulosic fibrous structure should exhibit a high degree of permeability to fluids. Also, the cellulosic fibrous structure must have sufficient tensile strength to prevent the cellulosic fibrous structure from tearing or shredding during ordinary use or when relatively small tensile forces are applied. The cellulosic fibrous structure must also be absorbent, so that liquids may be quickly absorbed and fully retained by the cellulosic fibrous structure at the end of the cleaning process. The cellulosic fibrous structure should also exhibit sufficient softness, so that it is tactilely pleasant and not harsh during use. The cellulosic fibrous structure should exhibit a high degree of opacity, so that it does not appear flimsy or of low quality to the user. Against this backdrop of competing interests, the cellulosic fibrous structure must be economical, so that it can be manufactured and sold for a profit, and yet is still affordable to the consumer.

Permeability is the property of a cellulosic fibrous structure which permits the flow of fluid through the interstitial regions of the fiber network. Permeability is inversely related to the basis weight and density of the structure. A cellulosic fibrous structure having relatively greater basis weight will therefore have a lower permeability for a given fluid.

Tensile strength is the ability of the cellulosic fibrous structure to retain its physical integrity during use. Tensile strength is controlled by the weakest link under tension in the cellulosic fibrous structure. The cellulosic fibrous structure will exhibit no greater tensile strength than that of any region in the cellulosic fibrous structure which is undergoing a tensile loading, as the cellulosic fibrous structure will fracture or tear through such weakest region.

The tensile strength of a cellulosic structure may be improved by increasing the basis weight of the cellulosic fibrous structure. However, increasing the basis weight requires more cellulosic fibers to be utilized in the manufacture, leading to greater expense for the consumer and requiring greater utilization of natural resources for the raw materials. Increasing the basis weight also significantly reduces the flow of fluids through the cellulosic fibrous structure, which corresponds to the structure's permeability.

Absorbency is the property of the cellulosic fibrous structure which allows it to attract and retain contacted fluids. Both the absolute quantity of fluid retained and the rate at which the cellulosic fibrous structure absorbs contacted fluids must be considered with respect to the desired end use of the cellulosic fibrous structure. Absorbency is influenced by the density of the cellulosic fibrous structure. If the cellulosic fibrous structure is too dense, the interstices between fibers may be too small and the rate of absorption may not be great enough for the intended use. If the interstices are too large, capillary attraction of contacted fluids is minimized and, due to surface tension limitations, fluids will not be retained by the cellulosic fibrous structure.

One compromise between the various aforementioned properties is to provide a cellulosic fibrous structure having mutually discrete zero basis weight apertures in an essentially continuous network having a particular basis weight. The discrete apertures represent regions of lower basis weight than the essentially continuous network, providing for bending perpendicular to the plane of the cellulosic fibrous structure, and hence increase the flexibility of the cellulosic fibrous structure. The apertures are circumscribed by the continuous network, which has a desired basis weight and which controls the tensile strength of the cellulosic fibrous structure.

Such apertured cellulosic fibrous structures are known in the prior art. For example, U.S. Pat. No. 3,034,180 issued May 15, 1962 to Greiner et al. discloses cellulosic fibrous structures having bilaterally staggered apertures and aligned apertures. Moreover, cellulosic fibrous structures having various shapes of apertures are disclosed in the prior art. For example, Greiner et al. discloses square apertures, diamond-shaped apertures, round apertures and cross-shaped apertures.

However, apertured cellulosic fibrous structures have several shortcomings. The apertures represent transparencies in the cellulosic fibrous structure and may cause the consumer to feel the structure is of lesser quality or strength than desired. The apertures are generally too large to retain fluids released by the emulsion, due to the limited surface tension of fluids typically encountered by the aforementioned tissue and towel products. Also, the basis weight of the network around the apertures must be increased so that sufficient tensile strength is obtained.

With regard to the cellulose structure aspect of the present invention, it is an object to provide a treated fibrous structure having high permeability without unduly sacrificing any of the other properties or requiring an uneconomical or undue use of natural resources. Specifically, it is an object of this invention to provide an emulsion treated cellulosic fibrous structure, such as paper, having relatively high and relatively low flow resistances to the drainage of the liquid carrier of the fibers in the forming apparatus and to proportion such flow resistances, relative to each other, to advantageously arrange the fibers in the low basis weight regions. Fibrous structures useful as the carrier herein, as well as methods and apparatus for making the structures, are described fully in U.S. Pat. No. 5,245,025, issued Sep. 14, 1993 to Trokhan et al., U.S. Pat. No. 5,503,715, issued Apr. 2, 1996 to Trokhan et al., and U.S. Pat. No. 5,534,326, issued Jul. 9, 1996 to Trokhan et al., the disclosure of each of which is incorporated herein by reference.

As is discussed in the '326 patent, by having regions of relatively high and relatively low resistances to flow present in the apparatus, one can achieve greater control over the orientation and pattern of deposition of the cellulosic fibers, and obtain cellulosic fibrous structures which provide the requisite fluid permeability. Generally, there is an inverse relation between the flow resistance of a particular region of the liquid pervious fiber retentive forming element and the basis weight of the region of the resulting cellulosic fibrous structure corresponding to such regions of the forming element. Thus, regions of relatively low flow resistance will produce corresponding regions in the cellulosic fibrous structure having a relatively high basis weight and vice versa, provided, of course, the fibers are retained on the forming element.

More particularly, the regions of relatively low flow resistance should be continuous so that a continuous high basis weight network of fibers results, and tensile strength is not sacrificed. The regions of relatively high flow resistance (which yield relatively low basis weight regions in the cellulosic fibrous structure and which orient the fibers) are preferably discrete, but may be continuous. These regions provide permeability to the structure, which allows fluid released from the emulsion to move from the wipe to the surface being cleaned.

Additionally, the size and spacing of the protuberances relative to the fiber length should be considered. If the protuberances are too closely spaced, the cellulosic fibers may bridge the protuberances and not be deposited onto the face of the forming element.

The forming element for the cellulosic fibrous structures is a forming belt having a plurality of regions discriminated from one another by having different flow resistances. The liquid carrier drains through the regions of the forming belt according to the flow resistance presented thereby. For example, if there are impervious regions, such as protuberances or blockages in the forming belts, no liquid carrier can drain through these regions and hence few or no fibers will be deposited in such regions.

The ratio of the flow resistances between the regions of high flow resistance and the regions of low flow resistance is thus critical to determining the pattern in which the cellulosic fibers entrained in the liquid carrier will be deposited. Generally, more fibers will be deposited in zones of the forming belt having a relatively lesser flow resistance, because more liquid carrier may drain through such regions. However, it is to be recognized that the flow resistance of a particular region on the forming belt is not constant and will change as a function of time.

By properly selecting the ratio of the flow resistance between discrete areas having high flow resistance and continuous areas of lower flow resistance, a cellulosic fibrous structure having a particularly preferred orientation of the cellulosic fibers can be accomplished. Particularly, the discrete areas may have cellulosic fibers of relatively lower basis weight than the essentially continuous region.

Figure 2:
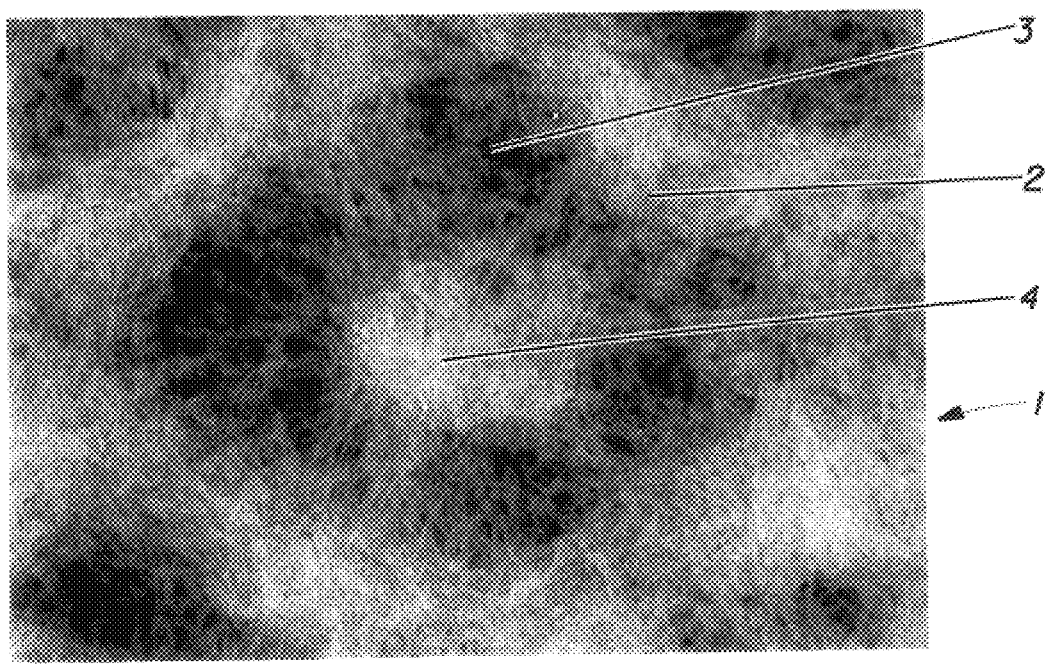
FIG. 2 is a top plan photomicrographic view (approximately 25× magnification) of the cellulosic fibrous structure shown in FIG. 1.

As illustrated in FIGS. 1 and 2, a cellulosic fibrous structure 1 useful as the carrier of the present invention has two regions: a first high basis weight region 2 and a second discrete low basis weight region 3. As shown in FIGS. 1 and 2, a third intermediate basis weight region 4 may also be present in the structure. In other embodiments, the cellulosic fibrous structure will have only a high basis weight region 2 and low basis weight regions 3. Each region 2 and 3 (and intermediate basis weight region 4, if present) is composed of cellulosic fibers which are approximated by linear elements. The fibers are components of the cellulosic fibrous structure 1 and have one very large dimension (along the longitudinal axis of the fiber) compared to the other two relatively very small dimensions (mutually perpendicular, and being both radial and perpendicular to the longitudinal axis of the fiber), so that linearity is approximated. While microscopic examination of the fibers may reveal two other dimensions which are small, compared to the principal dimension of the fibers, such other two small dimensions need not be substantially equivalent nor constant throughout the axial length of the fiber. It is only important that the fiber be able to bend about its axis, be able to bond to other fibers and be distributed by a liquid carrier.

The fibers comprising the cellulosic fibrous structure 1 may be synthetic, such as polyolefin or polyester; are preferably cellulosic, such as cotton linters, rayon or bagasse; and more preferably are wood pulp, such as soft woods (gymnosperms or coniferous) or hard woods (angiosperms or deciduous). As used herein, a cellulosic fibrous structure is considered "cellulosic" if the cellulosic fibrous structure comprises at least about 50 weight percent or at least about 50 volume percent cellulosic fibers, including but not limited to those fibers listed above. A cellulosic mixture of wood pulp fibers comprising softwood fibers having a length of about 2.0 to about 4.5 millimeters and a diameter of about 25 to about 50 micrometers, and hardwood fibers having a length of less than about 1 millimeter and a diameter of about 12 to about 25 micrometers have been found to work well for the cellulosic fibrous structures 1 described herein.

If wood pulp fibers are selected for the cellulosic fibrous structure 1, the fibers may be produced by any pulping process including chemical processes, such as sulfite, sulphate and soda processes; and mechanical processes such as stone groundwood. Alternatively, the fibers may be produced by combinations of chemical and mechanical processes or may be recycled. The type, combination, and processing of the fibers used are not critical to the present invention.

A cellulosic fibrous structure 1 useful in the present invention is macroscopically two-dimensional and planar, although not necessarily flat. The cellulosic fibrous structure 1 may have some thickness in the third dimension. However, the third dimension is very small compared to the actual first two dimensions or to the capability to manufacture a cellulosic fibrous structure 1 having relatively large measurements in the first two dimensions.

The cellulosic fibrous structure 1 may comprise a single lamina. Alternatively, it is to be recognized that two single laminae, either or both made according to the present invention, may be joined in face-to-face relation to form a unitary laminate. A cellulosic fibrous structure 1 according to the present invention is considered to be a "single lanina" if it is taken off the forming element as a single sheet having a thickness prior to drying which does not change unless fibers are added to or removed from the sheet. The cellulosic fibrous structure 1 may be later embossed, or remain nonembossed, as desired.

In addition to the cellulosic fibrous structure, the carrier may also comprise one or more hydrophobic materials which further assist in fluid flow out of and into the article. Such carriers are described in copending U.S. patent application Ser. No. 08/761,733, filed Dec. 5, 1996 by D. Cabell et al, the disclosure of which is incorporated by reference herein.

The cellulosic fibrous structure 1 may be defined by intensive properties which discriminate regions from each other. For example, the basis weight of the cellulosic fibrous structure 1 is one intensive property which discriminates the regions from each other. As used herein, a property is considered "intensive" if it does not have a value dependent upon the aggregation of values within the plane of the cellulosic fibrous structure 1. Examples of two dimensionally intensive properties include the density, projected capillary size, basis weight, temperature, compressive moduli, tensile moduli, fiber orientation, etc., of the cellulosic fibrous structure 1. As used herein properties which depend upon the aggregation of various values of subsystems or components of the cellulosic fibrous structure 1 are considered "extensive" in all three dimensions. Examples of extensive properties include the weight, mass, volume, and moles of the cellulosic fibrous structure 1. The intensive property most important to the cellulosic fibrous structure 1 described herein is the basis weight.

The cellulosic fibrous structure 1 has at least two distinct basis weights which are divided between two identifiable areas referred to as "regions" of the cellulosic fibrous structure 1. As used herein, the "basis weight" is the weight, measured in grams force, of a unit area of the cellulosic fibrous structure 1, which unit area is taken in the plane of the cellulosic fibrous structure 1. The size and shape of the unit area from which the basis weight is measured is dependent upon the relative and absolute sizes and shapes of the regions 2 and 3 having the different basis weights.

It will be recognized by one skilled in the art that within a given region 2 or 3, ordinary and expected basis weight fluctuations and variations may occur, when such given region 2 or 3 is considered to have one basis weight. For example, if on a microscopic level, the basis weight of an interstice between fibers is measured, an apparent basis weight of zero will result when, in fact, unless an aperture in the cellulosic fibrous structure 1 is being measured, the basis weight of such region 2 or 3 is greater than zero. Such fluctuations and variations are a normal and expected result of the manufacturing process.

It is not necessary that exact boundaries divide adjacent regions 2 or 3 of different basis weights, or that a sharp demarcation between adjacent regions 2 or 3 of different basis weights be apparent at all. It is only important that the distribution of fibers per unit area be different in different positions of the cellulosic fibrous structure 1 and that such different distribution occurs in a nonrandom, repeating pattern. Such nonrandom repeating pattern corresponds to a nonrandom repeating pattern in the topography of the liquid pervious fiber retentive forming element used to manufacture the cellulosic fibrous structure 1.

While it may be desirable from an opacity standpoint to have a uniform basis weight throughout the cellulosic fibrous structure 1, a uniform basis weight cellulosic fibrous structure 1 does not optimize other properties of the cellulosic fibrous structure 1. The different basis weights of the different regions 2 and 3 of a cellulosic fibrous structure 1 provide for different properties within each of the regions 2 and 3.

For example, the high basis weight regions 2 provide tensile load carrying capability, a preferred absorbent rate, and imparts opacity to the cellulosic fibrous structure 1. The low basis weight regions 3 provide for permeability of the structure to facilitate release of the fluid from the structure, storage of absorbed liquids when the high basis weight regions 2 become saturated and for economization of fibers.

Preferably, the nonrandom repeating pattern tesselates, so that adjacent regions 2 and 3 are cooperatively and advantageously juxtaposed. By being "nonrandom," the intensively defined regions 2 and 3 are considered to be predictable, and may occur as a result of known and predetermined features of the apparatus used in the manufacturing process. As used herein, the term "repeating" indicates pattern is formed more than once in the cellulosic fibrous structure 1.

Of course, it is to be recognized that if the cellulosic fibrous structure 1 is very large as manufactured, and the regions 2 and 3 are very small compared to the size of the cellulosic fibrous structure 1 during manufacture, i.e., varying by several orders of magnitude, absolute predictability of the exact dispersion and patterns between the regions 2 and 3 may be very difficult or even impossible and yet the pattern still be considered nonrandom. However, it is only important that such intensively defined regions 2 and 3 be dispersed in a pattern substantially as desired to yield the performance properties which render the cellulosic fibrous structure 1 suitable for its intended purpose.

The intensively discriminated regions 2 and 3 of the cellulosic fibrous structure 1 may be "discrete," so that adjacent regions 2 or 3 having the same basis weight are not contiguous. Alternatively, a region 2 or 3 may be continuous.

It will be apparent to one skilled in the art that there may be small transition regions having a basis weight intermediate the basis weights of the adjacent regions 2 or 3, which transition regions by themselves may not be significant enough in area to be considered as comprising a basis weight distinct from the basis weights of either adjacent region 2 or 3. Such transition regions are within the normal manufacturing variations known and inherent in producing a cellulosic fibrous structure 1 according to the present invention.

The size of the pattern of the cellulosic fibrous structure 1 may vary from about 3 to about 78 discrete regions 3 per square centimeter (from 20 to 500 discrete regions 3 per square inch), and preferably from about 16 to about 47 discrete regions 3 per square centimeter (from 100 to 300 discrete regions 3 per square inch).

It will be apparent to one skilled in the art that as the pattern becomes finer (having more discrete regions 2 or 3 per square centimeter) a relatively larger percentage of the smaller sized hardwood fibers may be utilized, and the percentage of the larger sized softwood fibers may be correspondingly reduced. If too many larger sized fibers are utilized, such fibers may not be able to conform to the topography of the forming apparatus which produces the cellulosic fibrous structure 1. If the fibers do not properly conform, such fibers may bridge various topographical regions of the apparatus, leading to a nonpatterned cellulosic fibrous structure 1. A cellulosic fibrous structure comprising about 100 percent hardwood fibers, particularly Brazilian eucalyptus, has been found to work well for a cellulosic fibrous structure 1 having about 31 discrete regions 3 per square centimeter (200 discrete regions 3 per square inch).

If the cellulosic fibrous structure 1 illustrated in FIG. 1 is to be used as a consumer product, such as toilet tissue, paper towels, wipes, or facial tissue, the high basis weight region 2 of the cellulosic fibrous structure 1 is preferably essentially continuous in two orthogonal directions within the plane of the cellulosic fibrous structure 1. It is not necessary that such orthogonal directions be parallel and perpendicular the edges of the finished product or be parallel and perpendicular to the direction of manufacture of the product, but only that tensile strength be imparted to the cellulosic fibrous structure in two orthogonal directions, so that any applied tensile loading may be more readily accommodated without premature failure of the product due to such tensile loading. Preferably, the continuous direction is parallel the direction of expected tensile loading of the finished product according to the present invention.

The high basis weight region 2 is essentially continuous, forming an essentially continuous network, for the embodiments described herein and extends substantially throughout the cellulosic fibrous structure 1. Conversely, the low basis weight regions 3 are discrete and isolated from one another, being separated by the high basis weight region 2.

An example of an essentially continuous network is the high basis weight region 2 of the cellulosic fibrous structure 1 of FIG. 1. Interruptions in the essentially continuous network are tolerable, albeit not preferred, so long as such interruptions do not substantially adversely affect the material properties of such portion of the cellulosic fibrous structure 1.

Conversely, the low basis weight regions 3 may be discrete and dispersed throughout the high basis weight essentially continuous network 2. The low basis weight regions 3 may be thought of as islands which are surrounded by a circumjacent essentially continuous network high basis weight region 2. The discrete low basis weight regions 3 also form a nonrandom, repeating pattern.

The discrete low basis weight regions 3 may be staggered in, or may be aligned in, either or both of the aforementioned two orthogonal directions. Preferably, the high basis weight essentially continuous network 2 forms a patterned network circumjacent the discrete low basis weight regions 3, although, as noted above, small transition regions may be accommodated.

Differences in basis weights (within the same cellulosic fibrous structure 1) between the high and low basis weight regions 2 and 3 of at least 25 percent are considered to be significant for the present invention. If a quantitative determination of basis weight in each of the regions 2 and 3 is desired, and hence a quantitative determination of the differences in basis weight between such regions 2 and 3 is desired, the quantitative methods, such as image analysis of soft X-rays as disclosed in U.S. Pat. No. 5,277,761, issued to Phan et al. on Jan. 11, 1994, may be utilized, which patent is incorporated herein by reference for the purpose of showing suitable methods to quantitatively determine the basis weights of the regions 2 and 3 of the cellulosic fibrous structure 1.

The area of a given low or intermediate basis weight region 3 or 4 may be quantitatively determined by overlaying a photograph of such region 3 or 4 with a constant thickness, constant density transparent sheet. The border of the region 3 or 4 is traced in a color contrasting to that of the photograph. The outline is cut as accurately as possible along the tracing and then weighed. This weight is compared to the weight of a similar sheet having a unit area, or other known area. The ratio of the weights of the sheets is directly proportional to the ratio of the two areas.

If one desires to know the relative surface area of two regions, such as the percentage surface area of an intermediate basis weight region 4 within a low basis weight region 3, the low basis weight region 3 sheet may be weighed. A tracing of the border of the intermediate basis weight region 4 is then cut from the sheet and this sheet is weighed. The ratio of these weights gives the ratio of the areas.

Generally, for purposes of the present invention, a cellulosic fibrous structure 1 is considered to have only two regions 2 and 3 if the presence of any intermediate basis weight region 4 is less than about 5 percent of the surface area of the entire low basis weight region 3, inclusive of any intermediate basis weight region 4, or if the basis weight of the intermediate basis weight region 4 is within about 15 percent of the basis weight of the low basis weight region 3.

The fibers of the two regions 2 and 3 may be advantageously aligned in different directions. For example, the fibers comprising the essentially continuous high basis weight region 2 may be preferentially aligned in a generally singular direction, corresponding to the essentially continuous network of the annuluses between adjacent protuberances of the forming belt (as shown in FIGS. 5–7 of U.S. Patent No. 5,534,326), as illustrated in FIG. 1.

This alignment provides for fibers to be generally mutually parallel and have a relatively high degree of bonding. The relatively high degree of bonding produces a relatively high tensile strength in the high basis weight region 2. Such high tensile strength in the relatively high basis weight region 2 is generally advantageous, because the high basis weight region 2 carries and transmits applied tensile loading throughout the cellulosic fibrous structure 1.

With regard to the fibrous structures useful herein, it is preferred that the aggregate surface area of the plurality of low basis weight regions (that is the surface area consisting of low basis weight regions) of the cellulosic fibrous structure is at least about 10% of the cellulosic fibrous structure's total surface area. More preferably, the aggregate surface area of the plurality of low basis weight regions is at least about 15%, still more preferably at least about 20%, of the cellulosic fibrous structure's total surface area. It is also preferred that the high basis weight, continuous region will have a basis weight at least about 30% greater, more preferably at least about 40% greater, still more preferably at least about 50% greater, than the basis weight of the low basis weight, discrete regions. Again, relative basis weight measurements can be made in accordance with the description set forth in U.S. Pat. No. 5,534,326, issued Jul. 9, 1996 to Trokhan, et al. and U.S. Pat. No. 5,277,761, issued to Phan et al. on Jan. 11, 1994.

In addition to fibers, the papermaking furnish used to make the cellulosic fibrous structures can have other components or materials added thereto as can be or later become known in the art. The types of additives desirable will be dependent upon the particular end-use of the tissue sheet contemplated. For example, in products such as toilet paper, paper towels, facial tissues, baby wipes and other similar products, wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins that have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene® 557H.

Polyacrylamide resins have also been found to be of utility as wet strength resins. These resins are described in U.S. Pat. Nos. 3,556,932 (Coscia et al), issued Jan. 19, 1971, and 3,556,933 (Williams et al), issued Jan. 19, 1971, both of which are incorporated by reference. One commercial source of polyacrylamide resins is American Cyanamid Co. of Stamford, Conn., which markets one such resin under the mark Parez® 631 NC.

Still other water-soluble cationic resins finding utility as wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit), CoBond 1000 (manufactured by National Starch and Chemical Company), and Parez® 750 (manufactured by American Cyanamide Co.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the fibrous structure, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the paper substrate.

In general, suitable starch binders for these fibrous structures are characterized by water solubility, and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn," H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

B. High Internal Phase Inverse Emulsion

The articles of the present invention comprise a carrier that is treated with a high internal phase inverse emulsion. The emulsion comprises: (1) a continuous solidified lipid phase; (2) an emulsifier that forms the emulsion when the lipid phase is fluid; and (3) an internal polar phase dispersed in the lipid phase. This emulsion ruptures when subjected to low shear during use, e.g., wiping of the skin or other surface, so as to release the internal polar phase.

1. External Lipid Phase

The continuous solidified lipid phase provides the essential stabilizing structure for the high internal phase inverse emulsions of the present invention. In particular, this continuous lipid phase is what keeps the dispersed internal phase from being prematurely released prior to use of the article, such as during storage.

The continuous lipid phase can comprise from about 2 to about 60% of the emulsion of the present invention. Preferably, this continuous lipid phase will comprise from about 5 to about 30% of the emulsion. Most preferably, this lipid phase will comprise from about 6 to about 15% of the emulsion.

The major constituent of this continuous lipid phase is a waxy lipid material. This lipid material is characterized by a melting point of about 30° C. or higher, i.e., is solid at ambient temperatures. Preferably, the lipid material has a melting point of about 50° C. or higher. Typically, the lipid material has a melting point in the range of from about 40° to about 80° C., more typically in the range of from about 50° to about 70° C.

Although this waxy lipid material is solid at ambient temperatures, it also needs to be fluid or plastic at those temperatures at which the high internal phase inverse emulsion is applied to the carrier. Moreover, even though the lipid material is fluid or plastic at those temperatures at which the emulsion is applied to the carrier substrate, it should still desirably be somewhat stable (i.e., minimal coalescence of emulsion micro-droplets) for extended periods of time at elevated temperatures (e.g., about 50° C. or higher) that are normally encountered during storage and distribution of the articles of the present invention. This lipid material also needs to be sufficiently brittle at the shear conditions of use of the article such that it ruptures and releases the dispersed internal polar phase. These lipid materials should also desirably provide a good feel to the skin when used in personal care products such as wet-like cleansing wipes and tissue used in perianal cleaning.

Suitable waxy lipid materials for use in the high internal phase inverse emulsion of the present invention include natural and synthetic waxes, as well as other oil soluble materials having a waxy consistency. As used herein, the term "waxes" refers to organic mixtures or compounds that are generally water-insoluble and tend to exist as amorphous or microcrystalline or crystalline solids at ambient temperatures (e.g., at about 25° C.). Suitable waxes include various types of hydrocarbons, as well as esters of certain fatty acids and fatty alcohols. They can be derived from natural sources (i.e., animal, vegetable or mineral) or they can be synthesized. Mixtures of these various waxes can also be used.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes.

Besides the waxy lipid material, the continuous lipid phase can include minor amounts of other lipophilic or lipid-miscible materials. These other lipophilic/lipid-miscible materials are typically included for the purpose of stabilizing the emulsion to minimize loss of the internal polar phase or for improving the aesthetic feel of the emulsion on the skin. Suitable materials of this type that can be present in the continuous lipid phase include hot melt adhesives such as Findley 193-336 resin, long chain alcohols such as cetyl alcohol, stearyl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharide polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinbefore described groups having a fluid consistency at or below about 37° C. By "solid polyol polyester" is meant a polyol polyester from the hereinbefore described groups having a plastic or solid consistency at or above about 37° C. Liquid polyol polyesters and solid polyol polyesters may be successfully employed as emollients and immobilizing agents, respectively, in emulsions of the present invention. In some cases, solid polyol polyesters may also provide some emolliency functionality.

2. Internal Polar Phase

Typically, the major component of the high internal phase inverse emulsions of the present invention is the dispersed internal polar phase. In preferred embodiments, the polar phase will contain a significant percentage of water, preferably at least about 60%, by weight of the emulsion, more preferably at least about 75%, by weight, still more preferably at least about 90%, by weight.

The internal polar phase can provide a number of different benefits when released. For example, in wet-like cleaning wipes for perianal cleaning where the internal polar phase is water, it is this released water that provides the primary cleansing action for these wipes.

In a preferred embodiment of the present invention, the internal polar phase (preferably comprising water as a major constituent) is a disinfecting polar phase comprising an antimicrobial compound, preferably an essential oil or an active thereof, and a bleach, preferably a peroxygen bleach. Disinfecting wipes comprising such an internal disinfecting polar phase provide effective disinfecting performance on a surface while being safe to the surface treated.

By "effective disinfecting performance" it is meant herein that the disinfecting wipes of the present invention allow significant reduction in the amount of bacteria on an infected surface. Indeed, effective disinfection may be obtained on various microorganisms including Gram positive bacteria like *Staphylococcus aureus*, and Gram negative bacteria like *Pseudomonas aeruginosa*, as well as on more resistant micro-organisms like fungi (e.g., *Candida albicans*) present on infected surfaces.

Another advantage of the disinfecting wipes according to the present invention is that besides the disinfection properties delivered, good cleaning is also provided as the disinfecting polar phase may further comprise surfactants and/or solvents.

An essential element of the preferred internal disinfecting polar phase is an antimicrobial compound typically selected from the group consisting of an essential oil and an active thereof, paraben (e.g., methyl paraben, ethyl paraben), glutaraldehyde and mixtures thereof. Essential oils or actives thereof are the preferred antimicrobial compounds to be used herein.

Suitable essential oils or actives thereof to be used herein are those essential oils which exhibit antimicrobial activity and more particularly antibacterial activity. By "actives of essential oils" it is meant herein any ingredient of essential oils that exhibits antimicrobial/antibacterial activity. A further advantage of said essential oils and actives hereof is that they impart pleasant odor to the disinfecting wipes according to the present invention without the need of adding a perfume. Indeed, the disinfecting wipes according to the present invention deliver not only excellent disinfecting performance on infected surfaces but also good scent.

Such essential oils include, but are not limited to, those obtained from thyme, lemongrass, citrus, lemons, oranges, anise, clove, aniseed, cinnamon, geranium, roses, mint, lavender, citronella, eucalyptus, peppermint, camphor, sandalwood and cedar and mixtures thereof. Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, terpineol, limonene, methyl salyciltate and mixtures thereof. Preferred actives of essential oils to be used herein are thymol, eugenol, verbenone, eucalyptol, carvacrol, limonene and/or geraniol. Thymol may be commercially available for example from Aldrich, eugenol may be commercially available for example from Sigma, Systems—Bioindustries (SBI)—Manheimer Inc.

Typically, the antimicrobial compound or mixtures thereof will be present in the internal polar phase at a level of from 0.001% to 5%, preferably from 0.001% to 3%, more preferably from 0.005% to 1%, by weight of total internal polar phase.

An important element of the internal disinfecting polar phase is a bleach or mixtures thereof. Any bleach known to those skilled in the art may be suitable to be used herein including any chlorine bleach as well as any peroxygen bleach. The presence of the bleach, preferably the peroxygen bleach, in the disinfecting wipes of the present invention contribute to the disinfection properties of the wipes.

Suitable chlorine bleaches to be used herein include any compound capable of releasing chlorine when said compound is in contact with water. Suitable chlorine bleaches include alkali metal dichloroisocyanurates as well as alkali metal hypohalites like hypochlorite and/or hypobromite. Preferred chlorine bleaches are alkali metal hypochlorites. Various forms of alkali metal hypochlorite are commercially available, for instance sodium hypochlorite.

Preferred bleaches for use herein are peroxygen bleaches, more particularly hydrogen peroxide, or a water soluble source thereof, or mixtures thereof. Hydrogen peroxide is particularly preferred.

Peroxygen bleaches like hydrogen peroxide are preferred herein as they are generally well accepted from an environmental point of view. For example the decomposition products of hydrogen peroxide are oxygen and water.

As used herein, a hydrogen peroxide source refers to any compound which produces perhydroxyl ions when said compound is in contact with water. Suitable water-soluble sources of hydrogen peroxide for use herein include percarbonates, persilicates, persulphates such as monopersulfate, perborates, peroxyacids such as diperoxydodecandioic acid (DPDA), magnesium perphthalic acid, dialkylperoxides, diacylperoxides, performed percarboxylic acids, organic and inorganic peroxides and/or hydroperoxides and mixtures thereof.

Typically, the bleach or mixtures thereof is present at a level of from 0.001% to 15% by weight of the total internal polar phase, preferably from 0.001% to 5%, and more preferably from 0.005% to 2%.

The internal disinfecting polar phase may further comprise a detersive surfactant or a mixture thereof. Typically, the surfactant or mixtures thereof is present at a level of from 0.001% to 40% by weight of the total internal polar phase, preferably from 0.01% to 10% and more preferably from 0.05% to 2%.

Suitable detersive surfactants to be used in the present invention include any surfactant known to those skilled in the art like nonionic, anionic, cationic, amphoteric and/or zwitterionic surfactants. Preferred detersive surfactants to be used herein are the amphoteric and/or zwitterionic surfactants.

Suitable amphoteric detersive surfactants to be used herein include amine oxides of the formula $R^1R^2R^3NO$, wherein each of $R^1$, $R^2$ and $R^3$ is independently a saturated, substituted or unsubstituted, linear or branched hydrocarbon chain having from 1 to 30 carbon atoms. Preferred amine oxide surfactants to be used according to the present invention are amine oxides of the formula $R^1R^2R^3NO$, wherein $R^1$ is an hydrocarbon chain having from 1 to 30 carbon atoms, preferably from 6 to 20, more preferably from 8 to 16, most preferably from 8 to 12, and wherein $R^2$ and $R^3$ are independently substituted or unsubstituted, linear or branched hydrocarbon chains having from 1 to 4 carbon atoms, preferably from 1 to 3 carbon atoms, and more preferably are methyl groups. $R^1$ may be a saturated, substituted or unsubstituted, linear or branched hydrocarbon chain. Suitable amine oxides for use herein are for instance natural blend $C_8$–$C_{10}$ amine oxides as well as $C_{12}$–$C_{16}$ amine oxides commercially available from Hoechst. Amine oxides are preferred herein as they deliver effective cleaning performance and further participate to the disinfecting properties of the disinfecting wipes herein.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolinium and sulfonium groups can be used. The typical anionic hydrophilic groups are carboxylates and sulfonates, although other groups such as sulfates, phosphonates, and the like can be used. A generic formula for some zwitterionic surfactants to be used herein is

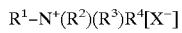

wherein $R^1$ is a hydrophobic group; $R^2$ and $R^3$ are each $C_1$–$C_4$ alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R^1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., hard surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

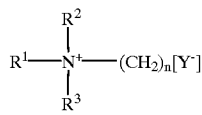

wherein $R^1$ is a hydrocarbon chain containing from 1 to 24 carbon atoms, preferably from 8 to 18, more preferably from 12 to 14, wherein $R^2$ and $R^3$ are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of $R^1$, $R^2$ and $R^3$ hydrocarbon chains is from 14 to 24 carbon atoms, or mixtures thereof.

Examples of particularly suitable betaine surfactants include $C_{12}$–$C_{18}$ alkyl dimethyl betaine such as coconutbetaine and $C_{10}$–$C_{16}$ alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

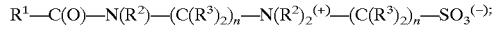

or

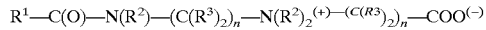

wherein each $R^1$ is a hydrocarbon, e.g. an alkyl group containing from 8 up to 20, preferably up to 18, more preferably up to 16 carbon atoms, each $R^2$ is either a hydrogen (when attached to the amido nitrogen), short chain alkyl or substituted alkyl containing from 1 to 4 carbon atoms, preferably groups selected from the group consisting of methyl, ethyl, propyl, hydroxy substituted ethyl or propyl and mixtures thereof, preferably methyl, each $R^3$ is selected from the group consisting of hydrogen and hydroxy groups and each n is a number from 1 to 4, preferably from 2 to 3, more preferably 3, with no more than one hydroxy group in any $(C(R^3)_2)$ moiety. The $R^1$ groups can be branched and/or unsaturated. The $R^2$ groups can also be connected to form ring structures. A surfactant of this type is a $C_{10}$–$C_{14}$ fatty acylamidopropylene-(hydroxypropylene)sulfobetaine that is available from the Sherex Company under the trade name "Varion CAS sulfobetaine"®.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are the hydrophobic nonionic surfactants having an HLB (hydrophilic-lipophilic balance) below 16 and more preferably below 15. Those hydrophobic nonionic surfactants have been found to provide good grease cutting properties.

Preferred nonionic surfactants for use herein are nonionic surfactants according to the formula $RO-(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and n and m are from 0.5 to 15, more preferably n+m is from 1 to 10 and n and m are from 0 to 10. The preferred R chains for use herein are the $C_8$ to $C_{22}$ alkyl chains. Accordingly, suitable hydrophobic nonionic surfactants for use herein are Dobanol R 91-2.5 (HLB=8.1; R is a mixture of $C_9$ and $C_{11}$ alkyl chains, n is 2.5 and m is 0), or Lutensol R TO3(HLB=8; R is a C13 alkyl chains, n is 3 and m is 0), or Lutensol R AO3 (HLB=8; R is a mixture of $C_{13}$ and $C_{15}$ alkyl chains, n is 3 and m is 0), or Tergitol R 25L3(HLB=7.7; R is in the range of $C_{12}$ to $C_{15}$ alkyl chain length, n is 3 and m is 0), or Dobanol R 23-3 (HLB=8.1; R is a mixture of $C_{12}$ and $C_{13}$ alkyl chains, n is 3 and m is 0), or Dobanol R 23-2(HLB=6.2; R is a mixture of $C_{12}$ and $C_{13}$ alkyl chains, n is 2 and m is 0), or Dobanol R 45-7(HLB= 11.6; R is a mixture of $C_{14}$ and $C_{15}$ alkyl chains, n is 7 and m is 0) Dobanol R 23-6.5(HLB=11.9; R is a mixture of $C_{12}$ and $C_{13}$ alkyl chains, n is 6.5 and m is 0), or Dobanol R 25-7

(HLB=12; R is a mixture of $C_{12}$ and $C_{15}$ alkyl chains, n is 7 and m is 0), or Dobanol R 91-5 (HLB=11.6; R is a mixture of $C_9$ and $C_{11}$ alkyl chains, n is 5 and m is 0), or Dobanol R 91-6 (HLB=12.5; R is a mixture of $C_9$ and $C_{11}$ alkyl chains, n is 6 and m is 0), or Dobanol R 91-8 (HLB=13.7; R is a mixture of $C_9$ and $C_{11}$ alkyl chains, n is 8 and m is 0), Dobanol R 91-10 (HLB=14.2; R is a mixture of $C_9$ to $C_{11}$ alkyl chains, n is 10 and m is 0), or mixtures thereof. Preferred herein are Dobanol R 91-2.5, or Lutensol R TO3, or Lutensol R AO3, or Tergitol R 25L3, or Dobanol R 23-3, or Dobanol R 23-2, or Dobanol R 23-10, or mixtures thereof. DobanolR surfactants are commercially available from SHELL. LutensolR surfactants are commercially available from BASF and the Tergitol R surfactants are commercially available from UNION CARBIDE.

Suitable anionic surfactants to be used herein include water soluble salts or acids of the formula $ROSO_3M$ wherein R is preferably a $C_6$–$C_{24}$ hydrocarbyl, preferably an alkyl or hydroxyalkyl having a $C_8$–$C_{20}$ alkyl component, more preferably a $C_8$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethylammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use herein are the alkyl benzene sulfonates, alkyl sulfates, alkyl alkoxylated sulfates, paraffin sulfonates and mixtures thereof.

The internal disinfecting polar phase according to the present invention has a pH of from 1 to 12, preferably from 3 to 10, and more preferably from 3 to 9. The pH can be adjusted by using alkalinizing agents or acidifying agents. Examples of alkalinizing agents are alkali metal hydroxides, such as potassium and/or sodium hydroxide, or alkali metal oxides such as sodium and/or potassium oxide. Examples of acidifying agents are organic or inorganic acids such as citric or sulfuric acid.

Solvents may be present in the internal disinfecting polar phase according to the present invention. These solvents will, advantageously, give an enhanced cleaning to the disinfecting wipes of the present invention. Suitable solvents for incorporation herein include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol® and mixtures thereof. A most preferred solvent for use herein is butyl carbitol®.

The internal disinfecting polar phase herein may further comprise other optional ingredients including radical scavengers, chelating agents, thickeners, builders, buffers, stabilizers, bleach activators, soil suspenders, dye transfer agents, brighteners, anti dusting agents, enzymes, dispersant, dye transfer inhibitors, pigments, perfumes, and dyes and the like.

Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole, p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy-4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein is di-tert-butyl hydroxy toluene, which is for example commercially available from SHELL under the trade name IONOL CP®.

Typically, the radical scavenger, or a mixture thereof, is present in the internal water phase up to a level of 5% by weight, preferably from 0.001% to 3% by weight, and more preferably from 0.001% to 1.5%.

Suitable chelating agents to be used herein may be any chelating agent known to those skilled in the art such as the ones selected from the group consisting of phosphonate chelating agents, amino carboxylate chelating agents or other carboxylate chelating agents, or polyfunctionally-substituted aromatic chelating agents and mixtures thereof.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelating agents are commercially available from Monsanto under the trade name DEQUEST®.

Polyfunctionally-substituted aromatic chelating agents may also be useful herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetate, diethylene triamine pentaacetate, diethylene triamine pentaacetate (DTPA), N-hydroxyethylethylenediamine triacetate, nitrilotri-acetate, ethylenediamine tetraproprionate, triethylenetetraaminehexa-acetate, ethanoldiglycine, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, dipicolinic acid and derivatives thereof, or mixtures thereof.

Typically, the chelating agent, or a mixture thereof, is present in the internal polar phase at a level of from 0.001% to 5% by weight, preferably from 0.001% to 3% by weight and more preferably from 0.001% to 1.5%.

The disinfecting wipes according to the present invention are suitable for disinfecting various surfaces including animate surfaces (e.g. human skin) as well as inanimate surfaces including any hard-surfaces.

Regardless of its composition, the internal polar phase will preferably comprise from about 67 to about 92% of the emulsion. Most preferably, the internal polar phase will comprise from about 82 to about 91% of the emulsion.

Where the internal polar phase comprises water as a major component, the internal phase can comprise water-soluble or dispersible materials that do not adversely affect the stability of the high internal phase inverse emulsion. One such material that is typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the internal water phase.

Other water-soluble or dispersible materials that can be present in the internal polar phase include thickeners and viscosity modifiers. Suitable thickeners and viscosity modifiers include polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Again, where water is a major constituent of the internal polar phase, water-soluble or dispersible materials that can be present in the internal phase include polycationic polymers to provide steric stabilization at the polar phase-lipid phase interface and nonionic polymers that also stabilize the emulsion. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the polar phase.

3. Emulsifier

Another key component of the high internal phase inverse emulsion of the present invention is an emulsifier. In the emulsions of the present invention, the emulsifier is included in an effective amount. What constitutes an "effective amount" will depend on a number of factors including the respective amounts of the lipid and internal polar phase components, the type of emulsifier used, the level of impurities present in the emulsifier, and like factors. Typically, the emulsifier comprises from about 1 to about 10% of the emulsion. Preferably, the emulsifier will comprise from about 3 to about 6% of the emulsion. Most preferably, the emulsifier will comprise from about 4 to about 5% of the emulsion. While the singular "emulsifier" is used to describe this component, more than one emulsifier may be used when forming the emulsion. Indeed, as discussed below, it may be desirable to utilize both a primary and a secondary emulsifier when certain materials are employed. Though not intended to limit the scope of the invention, where two emulsifiers are utilized, preferred is where the primary emulsifier comprises from about 1 to about 7%, more preferably from about 2 to about 5%, most preferably from about 2 to about 4%, by weight of the emulsion; and the secondary emulsifier comprises from about 0.5 to about 3%, more preferably from about 0.75 to about 2%, most preferably from about 0.75 to about 1.5%, by weight of the emulsion.

The emulsifier needs to be substantially lipid-soluble or miscible with the lipid phase materials, especially at the temperatures at which the lipid material melts. It also should have a relatively low HLB value. Emulsifiers suitable for use in the present invention have HLB values typically in the range of from about 2 to about 5 and can include mixtures of different emulsifiers. Preferably, these emulsifiers will have HLB values in the range of from about 2.5 to about 3.5.

Preferred emulsifiers for use in the present invention include silicone polymer emulsifiers such as alkyl dimethicone copolyols (e.g., Dow Coming Q2-5200 laurylmethicone copolyol). Such emulsifiers are described in detail in co-pending U.S. patent application Ser. No. 08/767,120, filed Jan. 14, 1997 by L. Mackey (Case 5653C), which is incorporated by reference herein.

Other suitable emulsifiers are described in co-pending U.S. patent application Ser. No. 08/336,456, filed Nov. 9, 1994 by L. Mackey et al. (Case 5478), and U.S. patent application Ser. No. 08/761,097, filed Dec. 5, 1996 by L. Mackey et al. (Case 5478R), both of which are incorporated by reference herein. Emulsifiers described therein include certain sorbitan esters, preferably the sorbitan esters of $C_{16}$–$C_{22}$ saturated, unsaturated or branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65) and sorbitan dipalmitates (e.g., SPAN® 40). Laurylmethicone copolyol is a particularly preferred emulsifier for use in the present invention. Other suitable emulsifiers described therein include certain glyceryl monoesters, preferably glyceryl monoesters of $C_{16}$–$C_{22}$ saturated, unsaturated or branched chain fatty acids such as glyceryl monostearate, glyceryl monopalmitate, and glyceryl monobehenate; certain sucrose fatty acid esters, preferably sucrose esters of the $C_{12}$–$C_{22}$ saturated, unsaturated, and branched chain fatty acids such as sucrose trilaurate and sucrose distearate (e.g., Crodesta® F10), and certain polyglycerol esters of $C_{16}$–$C_{22}$ saturated, unsaturated or branched fatty acids such as diglycerol monooleate and tetraglycerol monooleate. In addition to these primary emulsifiers, coemulsifiers can be used to provide additional water-in-lipid emulsion stability. Suitable coemulsifiers include phosphatidyl cholines and phosphatidyl choline-containing compositions such as the lecithins; long chain $C_{16}$–$C_{22}$ fatty acid salts such as sodium stearate, long chain $C_{16}$–$C_{22}$ dialiphatic, short chain $C_1$–$C_4$ dialiphatic quaternary ammonium salts such as ditallow dimethyl ammonium chloride and ditallow dimethyl ammonium methylsulfate; long chain $C_{16}$–$C_{22}$ dialkoyl(alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{16}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain $C_1$–$C_4$ dialiphatic, long chain $C_{16}$–$C_{22}$ monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries). Interfacial tension modifiers such as cetyl and stearyl alcohol for closer packing at the water-lipid interface can also be included.

Other emulsifiers useful in making the articles of the present invention include the high viscosity emulsifiers described in co-pending U.S. patent application Ser. No. 08/759,547, filed Dec. 5, 1996 by L. Mackey and B. Hird, which is incorporated by reference herein. These emulsifiers preferably have a viscosity at 55° C. of at least about 500 centipoise. (Viscosity can be measured using a Lab-Line Instruments Brookfield-type rotating disc viscometer.) That application describes specifically the use of emulsifiers such as those designated by The Lubrizol Corporation (Wickliffe, Ohio) as OS-122102, OS-121863, OS-121864, OS-80541J and OS-80691J, which are reaction products of (i) a hydrocarbyl-substituted carboxylic acid or anhydride (preferably a polyisobutylene-substituted succinic acid or anhydride); and (ii) an amine or alcohol, to form an ester or amide product. The materials, and methods for their manufacture, are described in U.S. Pat. No. 4,708,753, issued Nov. 24, 1987 to Forsberg [see especially Column 3, lines 32–38; and Column 8, line 10, to Column 26, line 68], and U.S. Pat. No. 4,844,756, issued Jul. 4, 1989 to Forsberg, both of which are incorporated by reference herein.

Other materials believed to be useful in the present invention include hydrocarbon-substituted succinic anhydrides such as those described in U.S. Pat. No. 3,215,707, issued Nov. 2, 1965 to Rense; U.S. Pat. No. 3,231,587, issued Jan. 25, 1996 to Rense; U.S. Pat. No. 5,047,175, issued to Forsberg on Sep. 10, 1991; and World Patent Publication Number WO 87/03613, published by Forsberg on Jun. 18, 1987. These publications are all incorporated by reference herein.

Still other materials useful as the emulsifier, particularly as a co-emulsifier with a high viscosity primary emulsifier, are ABA block copolymers of 12-hydroxystearic acid and polyethylene oxide. Such materials are described in U.S. Pat. No. 4,875,927, issued to T. Tadros on Oct. 24, 1989, which is incorporated by reference herein. A representative material of this class useful as an emulsifier herein is available from Imperial Chemical Industries PLC as Arlacel P135.

While all the above-described materials may be used as a single emulsifier, it may be desired to employ more than one emulsifier when forming the emulsion. In particular, where a high viscosity emulsifier is used, a certain "tacky" feel may result when the treated article is subjected to in-use shear pressures that break the emulsion. In this case, it may be desirable to use a relatively lower viscosity co-emulsifier with the primary emulsifier, to allow use of a lower amount of the main emulsifier, thereby alleviating tackiness. In one preferred embodiment of the present invention, a primary emulsifier available from Lubrizol (i.e., reaction product of polyisobutylene-substituted succinic acid and an amine) and a secondary emulsifier that is an ABA block copolymer of poly-12-hydroxystearic acid and polyethylene oxide (e.g., ICI's Arlacel P135) are used to provide an emulsion with improved water retention levels over time, as well as beneficial reduced tackiness (via reduction in level of primary emulsifier). The skilled artisan will recognize that different desired end-uses will dictate whether multiple emulsifiers are appropriate, and the appropriate relative amounts of each if appropriate. Such a determination will require only routine experimentation by the skilled artisan in view of the present disclosure.

4. Optional Emulsion Components

The high internal phase inverse emulsions of the present invention can also comprise other optional components typically present in moisture containing solutions of this type. These optional components can be present in either the continuous lipid phase or the internal polar phase and include perfumes, antimicrobial (e.g., antibacterial) actives, pharmaceutical actives, deodorants, opacifiers, astringents, skin moisturizers, and the like, as well as mixtures of these components. All of these materials are well known in the art as additives for such formulations and can be employed in effective, appropriate amounts in the emulsions of the present invention. A particularly preferred optional component that is included in the emulsions of wet-like cleansing wipes according to the present invention is glycerin as a skin conditioning agent.

The emulsion component of the articles of the present invention is described and claimed herein in terms of components, and corresponding amounts of the components, that are present after emulsion formation. That is, when the stable emulsion is formed and applied to the carrier. It is understood that the description (components and amounts) of the emulsion also encompasses emulsions formed by combining the described components and levels, regardless of the chemical identity of the components after emulsification and application to the carrier.

C. Other Optional Article Components

Besides the high internal phase inverse emulsion, there are other optional components that can be included in the articles of the present invention, typically for the purpose of improving the cleaning performance of the article when the internal polar phase of the emulsion is released. Certain of these optional components cannot be present in the emulsion at significant levels (e.g., greater than 2% of the internal phase) because they can cause premature disruption of the emulsion. These include various anionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, ampholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion. For example, an aqueous solution of these high HLB detergent surfactants can be applied to the carrier either before or after application of the emulsion to the carrier. During wiping, the emulsion is disrupted, releasing the polar phase components so that they can then be combined with the high HLB detergent surfactant to provide improved hard surface cleaning.

Though the description of the invention generally relates to applying a single water-in-lipid emulsion to the carrier, it is recognized that two or more different emulsions may be utilized in preparing a single article. In such embodiments, the emulsions may differ in a variety of ways, including but not limited to, the ratio of the internal polar phase and the external lipid phase, the emulsifiers used, the components used for either or both of the internal and lipid phases, and the like. Utilization of multiple emulsions in one article may be particularly desirable when two or more components are incompatible with each other, but can each be included in a separate emulsion. Alternatively, if a particular reaction is desired at the time of use, the reactants can be provided in separate emulsions. Upon shearing of the emulsions during use, the desired reaction will occur. For example, where foaming is desired during the wiping processes, a mild acid can be incorporated in the internal polar phase of one emulsion, while bicarbonate is incorporated in the internal polar phase of a second emulsion. Upon shearing of the emulsions during use, the reactants interact to provide the desired foam.

D. Preparation of Emulsion Treated Articles

In preparing the articles according to the present invention, the high internal phase emulsion is initially formulated. Typically, this is achieved by blending or melting together the lipid phase components and the emulsifier. The particular temperature to which this lipid/emulsifier mixture is heated will depend on the melting point of the lipid phase components. Typically, this lipid/emulsifier mixture is heated to a temperature in the range from about 50° to about 90° C., preferably from about 70° to about 80° C., prior to being mixed, blended or otherwise combined with the internal polar phase components. The melted lipid/emulsifier mixture is then blended with the internal polar phase components and then mixed together, typically under low shear conditions to provide the emulsion.

This high internal phase inverse emulsion is then applied in a fluid or plastic state at the temperatures indicated above to a carrier that will provide the article with the requisite permeability. Any of a variety of methods that apply materials having a fluid or plastic consistency can be used to apply this emulsion. Suitable methods include spraying, printing (e.g., flexographic or screen printing), coating (e.g., gravure coating), extrusion, or combinations of these application techniques, e.g. spraying the detergent surfactant on the paper web, followed by gravure coating of the emulsion on the detergent treated web.

The emulsion can be applied either to one or both surfaces of the carrier, or it can be applied to the inner and/or outer surface(s) of the plies that makes up the carrier. For example, in the case of a two ply carrier, the emulsion can be applied to the inner surface of one or both of the plies, leaving the outside surface of the carrier free of the emulsion. This carrier design minimizes transfer of wax and emulsifier to the surface being cleaned, which is especially desirable when higher loadings of emulsion are used to provide more liquid for cleaning. For example, to provide the level of liquid of a typical wipe for cleaning hard surfaces, a loading of emulsion of five times the weight of the carrier or greater might be used. The application of the emulsion to both sides of the carrier can be either sequential or simultaneous. Once the emulsion has been applied to the carrier, it is allowed to cool and solidify to form a solidified, typically discontinuous coating or film on the surface of the carrier. However, the emulsion can be applied to the carrier such that a continuous or discontinuous coating results.

The emulsion can be applied nonuniformly to the surface (s) of the carrier. By "nonuniform" is meant that the amount, pattern of distribution, etc. of the emulsion can vary over the surface(s) of the material being treated. For example, some portions of the surface of the carrier can have greater or lesser amounts of the emulsion, including portions of the surface that do not have any emulsion (i.e., application results in discontinuous emulsion coating). The high internal phase inverse emulsion can be applied to the carrier at any point after it has been dried. For example, the emulsion can be applied to the carrier after it has been creped from a Yankee dryer. Usually, it is preferred to apply the emulsion to the paper web as it is being unwound from a parent roll and prior to being wound up on smaller, finished product rolls.

Figure 3:
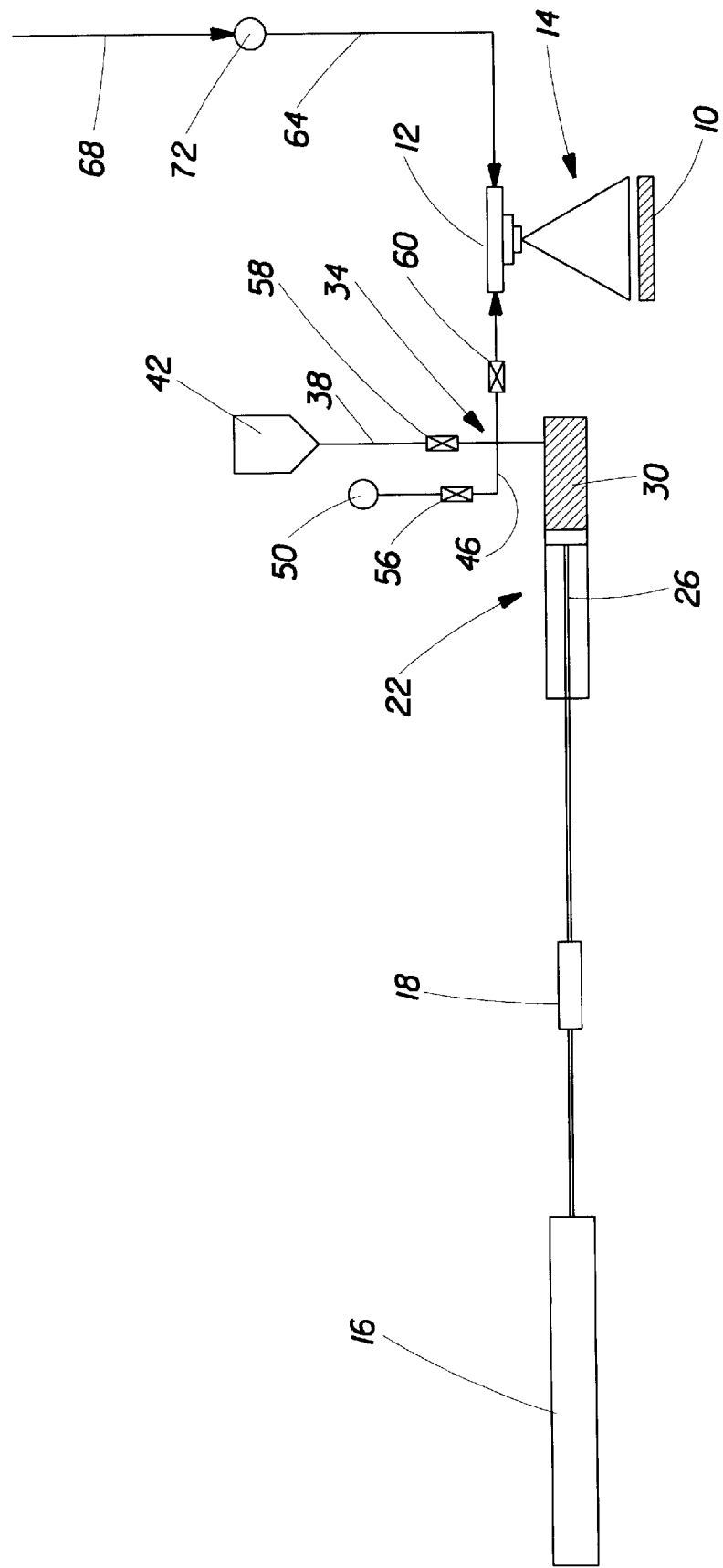
FIG. 3 is a schematic representation illustrating a spray system for applying the high internal phase inverse emulsions of the present invention to a carrier such as a treated paper web.

In applying high internal phase inverse emulsions to the carriers, spray and gravure coating methods are usually preferred. FIG. 3 illustrates one such preferred method where the emulsion is sprayed onto a carrier 10. Referring to FIG. 3, this spray system has a spray head 12 that applies a dispersed spray 14 of the emulsion onto carrier 10.

This spray system is actuated by an assembly that consists of a ball screw drive 16 that is connected by coupling 18 to a piston 26 of hydraulic cylinder 22. A portion of cylinder 22 is shown in FIG. 3 as being filled with the high internal phase inverse emulsion as indicated by 30. Cylinder 22 is heated to keep emulsion 30 in a fluid or plastic state.

Emulsion 30 enters cylinder 22 via a 4-way coupling 34 that has a line 38 connected to a heated filling port 42. Coupling 34 also has a line 46t hat is connected to pressure gauge 50 and spray head 12. There are three valves indicated as 56, 58 and 60 that control the flow of the emulsion in lines 38 and 46. The spray system shown in FIG. 3 also has a line 64 connected to spray head 12 that allows air indicated generally as 68 to be admitted to the spray head. Line 64 also has a pressure gauge and regulator 72 for controlling and measuring the air pressure in line. Lines 64 and 46 are heated to maintain the emulsion in a molten state prior to application to the carrier.

To fill cylinder 22 with emulsion 30, valves 56 and 60 are closed and valve 58 is opened. Ball screw drive 16 is actuated so that piston 26 moves to the left. The vacuum created in cylinder 22 draws the emulsion from filling port 42 through line 38 and into cylinder 22. To provide emulsion from cylinder 22 to spray head 12, valve 58 is closed and valves 56 and 60 are opened. The ball screw drive 16 is actuated so that piston 26 moves to the right. This forces emulsion 30 out of cylinder 22 and into line 46 of coupling 34. The emulsion then passes through valve 60 and into the spray head 12 where it is dispersed by incorporation of air from line 64 to provide dispersed spray 14 that is then applied to carrier 10.

Figure 4:
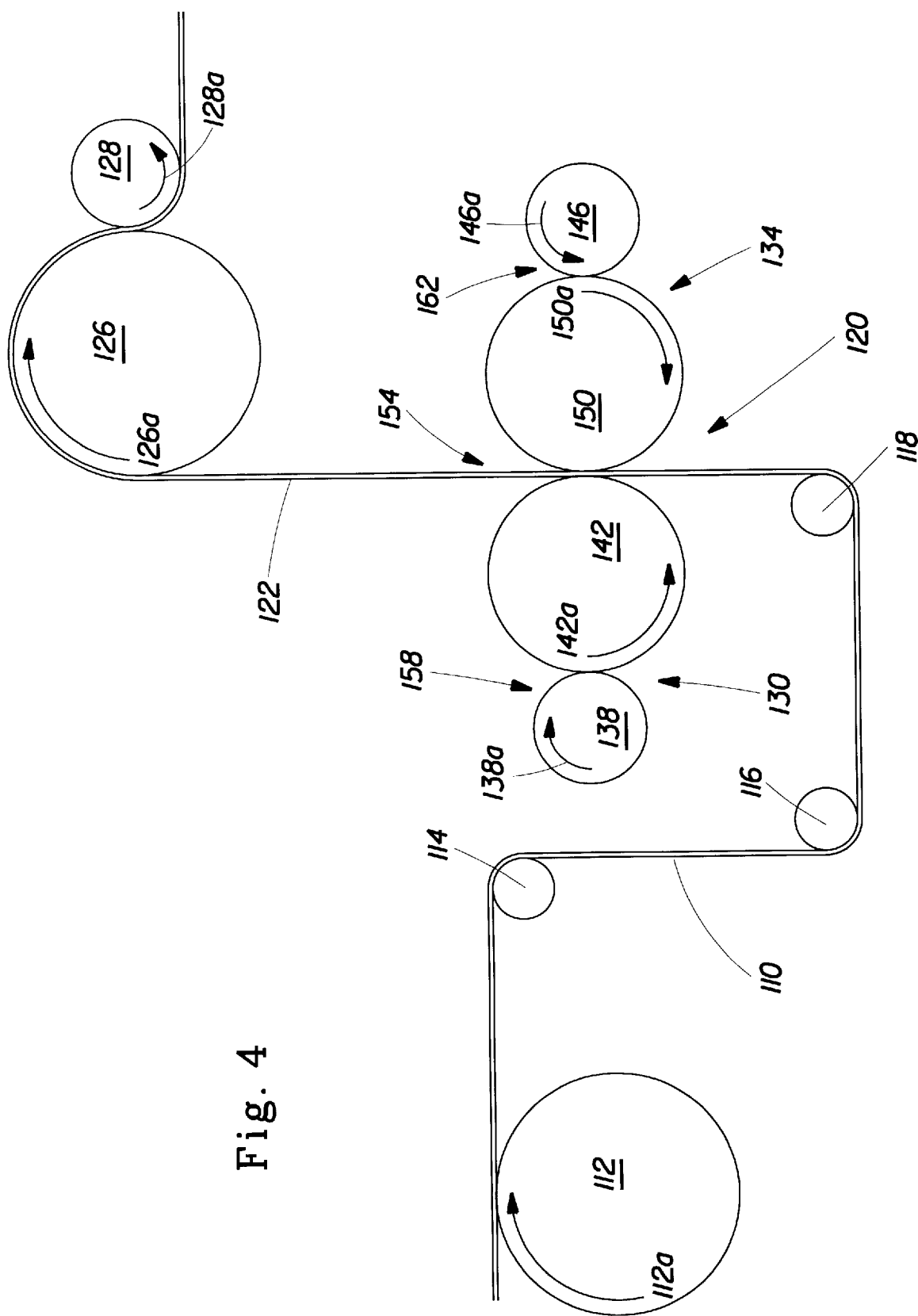
FIG. 4 is a schematic representation illustrating a system for applying the high internal phase inverse emulsions of the present invention by gravure coating to a carrier such as a treated paper web.

FIG. 4 illustrates an alternative method for applying the high internal phase inverse emulsion involving a flexible rotogravure coating system. Referring to FIG. 4, a carrier 110 is unwound from parent tissue roll 112 (rotating in the direction indicated by arrow 112a) and advanced around turning rolls 114, 116 and 118. From turning roll 118, carrier 110 is advanced to a gravure coating station indicated generally as 120 where the emulsion is then applied to both sides of the carrier. After leaving station 120, carrier 110 becomes a treated web indicated by 122. Treated web 122 is advanced to surface rewinder roll 126 (rotating in the direction indicated by arrow 126a) and then wound up on finished product roll 128 (rotating in the direction indicated by arrow 128a).

Station 120 comprises a pair of heated linked gravure presses 130 and 134. Press 130 consists of a smaller anilox cylinder 138 and a larger print plate cylinder 142; press 134 similarly consists of a smaller anilox cylinder 146 and a larger print plate cylinder 150. Anilox cylinders 138 and 146 each have a ceramic or chrome surface, while print plate cylinders 142 and 150 each have a relief patterned rubber, urethane, or photopolymer surface. These anilox and print plate cylinders rotate in the directions indicated by arrows 138a, 142a, 146a and 150a, respectively. As shown in FIG. 4, print plate cylinders 142 and 150 are opposed to one another and provide a nip area indicated by 154 through which carrier 110 passes.

Hot, molten (e.g., 60° C.) emulsion is pumped to or sprayed onto each of these linked gravure presses 130 and 134 at the nip areas indicated by arrows 158 and 162, respectively, at a constant volumetric flow rate. (Emulsion delivered to presses 130 and 134 may be the same or different.) In other words, the emulsion is added to the linked gravure presses 130 and 134 at the same rate as the emulsion is being applied to the carrier 110. This eliminates emulsion "build-up" in the system. As anilox cylinders 138 and 146 rotate in the directions indicated by arrows 138a and 146a, they act as rotating doctor blades to spread the emulsion evenly across the surfaces of print plate cylinders 142 and 150, respectively, and to remove excess emulsion from the print plates of cylinders 142 and 150.

The emulsion that is spread onto print plate cylinders 142 and 150 (rotating in the opposite direction as indicated by arrows 142a and 150b) is then transferred to both sides of carrier 110 at nip area 154. The amount of the emulsion transferred to carrier 110 can be controlled by: (1) adjusting the width of nip area 154 between print plate cylinders 142 and 150; (2) adjusting the width of nip areas 158 and 162 between anilox/print plate cylinder pairs 138/142 and 146/150; (3) the print image relief (i.e., valley depth) of the print plate on cylinders 142 and 150; (4) the print area (i.e., valley area) of the print plate on cylinders 142 and 150; and/or (5) the print pattern of the print plate on cylinders 142 and 150.

III. Illuctrative Examples

Example 1

This example illustrates the preparation of a disinfecting/cleaning wipe article comprising an emulsion applied to a cellulosic fibrous substrate (carrier) having variable basis weight zones. The emulsion is added to either or both sides of the fibrous cellulosic substrate. Preferably the carrier comprises two such substrates, wherein the emulsion is applied between the two plies.

A) Carrier Preparation

The carrier is a tissue/towel paper substrate. The base paper is a 100% NSK, non-layered sheet with a basis weight of 20 lbs/ream. The paper has a continuous high basis weight zone (corresponding to region 2 of FIGS. 1 and 2), a plurality of low basis weight and intermediate basis weight zones (corresponding to regions 3 and 4, respectively, of FIGS. 1 and 2). The paper is produced according to the teachings of U.S. Pat. No. 5,506,715 (Trokhan, et al) with the following specifics:

1) The forming wire contains 100 protuberances per square inch.

2) The protuberances occupy about 50% of the surface area of the forming wire.

3) The protuberances extend above the forming wire reinforcing structure about 0.004 inches.

4) The aperatures of each protuberance occupy about 10% of the surface area of the forming wire.

5) In the wet end of the papermaking process, a 2% amino-silicone (available from General Electric as CM 22666D1) is injected into the NSK pulp slurry at a ratio of 0.004 lbs. of amino silicone solids per pound of dry paper.

6) In the wet end of the papermaking process, 1% of Kymene® 557H (Available from Hercules Inc.) is injected into the NSK pulp slurry at a ratio of 20 pounds of Kymene solids per ton of dry paper.

The paper carrier is now ready for emulsion addition, with the variable basis weight zones providing the channels for fluid flux during product use.

B) Emulsion Preparation

A 1000 g batch of an emulsion having 88.75% internal polar phase (consisting primarily of water) is prepared from the ingredients shown in Table I.

TABLE I

|  | Amount (gm) | Percentage |
|---|---|---|
| Lipid Phase Ingredients: | | |
| Strahl & Pitsch SP983 | 40 | 4.0 |
| Petrolatum | 10 | 1.0 |
| Strahl & Pitsch SP1190 | 40 | 4.0 |
| Dow Q2-5200 | 20 | 2.0 |

TABLE I-continued

|  | Amount (gm) | Percentage |
|---|---|---|
| Glycomul TS | 2.5 | 0.25 |
| Polar Phase Ingredients: | | |
| Distilled Water | 826.3 | 82.63 |
| HEDP | 0.2 | 0.02 |
| Hydrogen Peroxide | 8.0 | 0.8 |
| Ethanol | 50 | 5.0 |
| C-12 Amine Oxide | 1.0 | 0.10 |
| Geraniol | 1.5 | 0.15 |
| Thymol | 0.5 | 0.05 |

To formulate the internal polar phase, all polar phase components are mixed together and then heated to 140° F. (45.8° C.). Separately, the lipid phase ingredients are heated, with mixing, to a temperature of about 140° F. until melted. The polar and lipid phase components are then combined in a stainless steel vessel and mixed with a Hobart Model 100-C mixer on the low speed setting while allowing the ingredients to cool slowly. Mixing continues until the emulsion forms. Emulsion formation is evidenced by an increase in viscosity above 2000 centipoise as measured with a Lab-Line Instruments rotating disc viscometer.

C) Applying Emulsion to Paper Carrier

The emulsion prepared in step B is applied to the paper carrier described in step A using a rotogravure printing process essentially the same as that shown in FIG. 4, except that only one gravure press (130) is utilized. (Also, rewinder roll 126 is not utilized in preparing the article described by this example.) The emulsion is heated to a temperature of 135° F. so that it is fluid or molten. A positive displacement pump moves the emulsion to the gravure press 130 at the nip area indicated by arrow 158 at a constant volumetric flow rate of 380 ml/minute. Anilox cylinder 138 spreads the emulsion evenly across the surface of the print cylinder 142 (rotating at about 40 feet per minute). Cylinder 142 then transfers the emulsion to one side of web 110 (cylinder 150 is used as a back-up cylinder to maintain constant impression on web 110). The coated paper carrier 122 is then perforated, folded and sealed (apparatus for performing these functions is not depicted in FIG. 4) to yield finished product wipe. After folding and sealing, the emulsion coats both internal sides of the paper carrier at about 700% add-on, by dry weight of the paper carrier, to provide an article of the present invention.

Example 2

This example illustrates the preparation of a moisture releasing toilet tissue comprising an emulsion applied to a paper substrate with variable basis weight zones. The emulsion is added to either or both sides of the carrier, or between two plies.

A) Carrier Preparation

The carrier is a tissue/towel paper substrate. The base paper is 60% NSK (i.e., Northern Softwood Kraft) and 40% eucalyptus in a non-layered sheet with a basis weight of 9.5 lbs/ream. The paper has a continuous high basis weight zone (corresponding to region 2 of FIGS. 1 and 2), a plurality of low basis weight and intermediate basis weight zones (corresponding to regions 3 and 4, respectively, of FIGS. 1 and 2). The paper is produced according to the teachings of U.S. Pat. No. 5,506,715 (Trokhan, et al) with the following specifics:

1) The forming wire contains 200 protuberances per square inch.
2) The protuberances occupy about 50% of the surface area of the forming wire.
3) The protuberances extend above the forming wire reinforcing structure about 0.008 inches.
4) The aperatures of each protuberance occupy about 10% of the surface area of the forming wire.
5) In the wet end of the papermaking process, 2% Parez® 750B (Available from Hercules Inc.) is injected into the pulp slurry at a ratio of 3 pounds of Parez solids per ton of dry paper.

The paper carrier is now ready for emulsion addition, with the variable basis weight zones providing the channels for fluid flux during product use.

B) Emulsion Preparation

A 1000 g batch of an emulsion (88.65% internal phase) is prepared from the ingredients shown in Table II.

TABLE II

|  | Amount (gm) | Percentage |
|---|---|---|
| Lipid Phase Ingredients: | | |
| Yellow Ceresine Wax (Strahl & Pitsch SP983) | 40 | 4.0 |
| Petrolatum (Fisher) | 10 | 1.0 |
| White Ozokerite Wax (Strahl & Pitsch SP1190) | 40 | 4.0 |
| Dow Corning 5200 | 20 | 2.0 |
| Polar Phase Ingredients: | | |
| EDTA | 1.0 | 0.1 |
| Glycomul TS | 2.5 | 0.25 |
| Glydent Plus | 3.0 | 0.3 |
| Distilled Water | 883.5 | 88.35 |

To formulate the internal polar phase, all polar phase components are mixed together and then heated to 140° F. (45.8° C.). Separately, the lipid phase ingredients are heated, with mixing, to a temperature of about 140° F. until melted. The polar and lipid phase components are then combined in a stainless steel vessel and mixed with a Hobart Model 100-C mixer on the low speed setting while allowing the ingredients to cool slowly. Mixing continues until the emulsion forms. Emulsion formation is evidenced by an increase in viscosity above 2000 centipoise as measured with a Lab-Line Instruments rotating disc viscometer.

C) Applying Emulsion to Paper Carrier

The emulsion prepared in step B is applied to the paper carrier described in step A using a rotogravure printing process essentially the same as that shown in FIG. 4, except that only one gravure press (130) is utilized. The emulsion is heated to a temperature of 135° F. so that it is fluid or molten. A positive displacement pump moves the emulsion to the gravure press 130 at the nip area indicated by arrow 158 at a constant volumetric flow rate of 110 ml/minute. Anilox cylinder 138 spreads the emulsion evenly across the surface of the print cylinder 142 (rotating at about 40 feet per minute). Cylinder 142 then transfers the emulsion to one side of web 110 (cylinder 150 is used as a back-up cylinder to maintain constant impression on web 110). After being combined with a second ply, the emulsion is contained in the interior at about 200% add-on, by dry weight of the paper carrier, to provide an article of the present invention.

What is claimed is:

1. An article, which comprises:
   a. a carrier comprising a cellulosic fibrous structure having at least a first region of relatively high basis weight that comprises an essentially continuous network and a second region of a plurality of mutually discrete regions of relatively low basis weight which are circumscribed by the high basis weight first region; and b. an emulsion applied to the carrier, the emulsion comprising:
   (1) from about 2 to about 60% of a continuous, solidified lipid phase comprising a waxy lipid material having a melting point of about 30° C. or higher;
   (2) from about 39 to about 97% of an internal polar phase dispersed in the lipid phase; and
   (3) an effective amount of an emulsifier that forms the emulsion when the lipid phase is in a fluid state.

2. The article of claim 1 wherein the emulsion comprises from about 5 to about 30% lipid phase and from about 67 to about 92% polar phase.

3. The article of claim 2 wherein the emulsion comprises from about 6 to about 15% lipid phase and from about 82 to about 91% polar phase.

4. The article of claim 1 wherein the emulsion's internal polar phase comprises at least 60% water.

5. The article of claim 4 wherein the emulsion's internal polar phase comprises at least 75% water.

6. The article of claim 1 wherein the waxy lipid material has a melting point in the range of from about 40° to about 80° C.

7. The article of claim 6 wherein the waxy lipid material has a melting point in the range of from about 60° to about 70° C.

8. The article of claim 1 wherein the waxy lipid material is selected from the group consisting of animal waxes, vegetable waxes, mineral waxes, synthetic waxes and mixtures thereof.

9. The article of claim 8 wherein said waxy lipid material is selected from the group consisting of beeswax, carnauba, spermaceti, lanolin, shellac wax, candelilla, paraffin, petrolatum, microcrystalline wax, white ceresine wax, yellow ceresine wax, white ozokerite wax, polyethylene waxes, chlorinated naphthalenes, and mixtures thereof.

10. The article of claim 9 wherein the waxy lipid material is selected from the group consisting of beeswax, lanolin, candelilla, petrolatum, microcrystalline wax, yellow ceresine wax, white ozokerite, polyethylene waxes, and mixtures thereof.

11. The article of claim 1 wherein said emulsifier comprises from about 1 to about 10% of said emulsion.

12. The article of claim 11 wherein said emulsifier comprises from about 3 to about 6% of said emulsion and is selected from group consisting of sorbitan monooleate, sorbitan monoisostearate, sorbitan sesquioleate, sorbitan stearates, sorbitan triooleate, sorbitan dipalmitates, glyceryl monostearate, glyceryl monopalmitate, glyceryl monobehenate, sucrose trilaurate, sucrose distearate, diglycerol monooleate, tetraglycerol monooleate, and mixtures thereof.

13. The article of claim 11 a wherein said emulsifier has the following general formula:

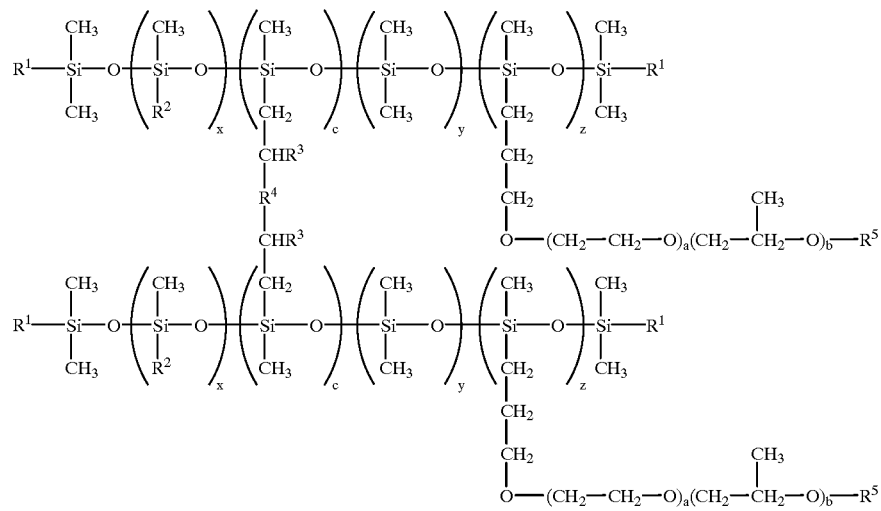

wherein $R^1$ is an aliphatic radical having from 1 to 25 carbon atoms which can be different for each different location; $R^2$ is an aliphatic radical having from 2 to 25 carbon atoms; $R^3$ is independently selected from hydrogen and aliphatic radicals having 1 to 3 carbon atoms which can be different for each different location; $R^4$ is an organic or organosiloxane group which contains no hydrolyzable bonds, is not adversely reactive with the ingredients the emulsifier is to stabilize and does not interfere with the formation of the organopolysiloxane-polyoxyalkylene; $R^5$ is a terminal group which is not adversely reactive with the ingredients the emulsifier is to stabilize and does not interfere with the formation of the organopolysiloxane-polyoxyalkylene; x is 1 to 100; y is 0 to 600; z is 1 to 100; x+y+z is at least 30; a is 4 to 40; b is 0 to 40; c is 0 to 5; the ratio of a:b is 20:80 to 100:0.

14. The article of claim 13 wherein $R^1$ is methyl; $R^2$ is $C_8$ to $C_{18}$ alkyl, $R^3$ is hydrogen; $R^4$ is —$(CH_3)_2$—Si—O—Si$(CH_3)_2$—; $R^5$ is hydrogen; x is 5 to 60; y is 0 to 150; z is 1 to 15; a is 10 to 30; b is 10to 30; c is 0 to 1.

15. The article of claim 14 wherein $R^2$ is $C_{12}$ alkyl; x is 30 to 60; y is 0; z is 1 to 2; c is 0 to 1; the ratio of a:b is from 50:50 to 100:0.

16. The article of claim 13 wherein $R^2$ is $C_{16}$ alkyl; x is 5 to 50; y is 25 to 150; c is 0; z is 1 to 15; the ratio of a:b is from 40:60 to 70:30.

17. The article of claim 1 wherein said emulsifier has a viscosity of at least about 500 centistokes at 25° C.

18. The article of claim 17 wherein said emulsifier has a viscosity of from about 1000 to about 30,000 centistokes at 25° C.

19. The article of claim 1 wherein the emulsion further comprises a component selected from the group consisting of perfumes, antimicrobials, detersive surfactants, pharmaceutical actives, deodorants, opacifiers, astringents, insect repellents, bleaches, radical scavengers, chelating agents, thickeners, builders, buffers, stabilizers, bleach activators, soil suspenders, dye transfer agents, brighteners, anti dusting agents, enzymes, dispersants, dye transfer inhibitors, pigments, dyes, and mixtures thereof.

20. The article of claim 19 wherein the emulsion comprises a component selected from the group consisting of antimicrobials, detersive surfactants, bleaches, and mixtures thereof.

21. The article of claim 1 wherein at least two different emulsions are applied to said carrier.

22. The article of claim 1 wherein the aggregate surface area of the plurality of low basis weight regions of the cellulosic fibrous structure is at least about 10% of the cellulosic fibrous structure's total surface area.

23. The article of claim 22 wherein the aggregate surface area of the plurality of low basis weight regions is at least about 20% of the cellulosic fibrous structure's total surface area.

24. The article of claim 22 wherein the basis weight of the high basis weight region is at least about 25% greater than the basis weight of the low basis weight regions.

25. The article of claim 24 wherein the basis weight of the high basis weight region is at least about 35% greater than the basis weight of the low basis weight regions.

26. The article of claim 25 wherein the basis weight of the high basis weight region is at least about 50% greater than the basis weight of the low basis weight regions.

27. The article of claim 1 wherein the carrier comprises a cellulosic fibrous structure comprising at least two regions disposed in a nonrandom, repeating pattern:
   a. a first essentially continuous load bearing network region; and
   b. a plurality of mutually discrete second regions having fewer fibers per unit area than said first region.

28. The article of claim 1 wherein the carrier further comprises a third region comprising a plurality of mutually discrete regions having a basis weight intermediate to the high basis weight first region and the low basis weight second region, wherein each mutually discrete region having an intermediate basis weight is circumscribed by a discrete low basis weight region.

29. An article, which comprises:
   a. a carrier comprising a cellulosic fibrous structure having at least a first region of relatively high basis weight that comprises an essentially continuous network and a second region of a plurality of mutually discrete regions of relatively low basis weight which are circumscribed by the high basis weight first region; wherein the aggregate surface area of the plurality of mutually discrete regions of relatively low basis weight comprise at least about 10% of the cellulosic fibrous structure's total surface area and the basis weight of the relatively high basis weight first region is at least about 25% greater than the basis weight of the second region of mutually discrete regions of relatively low basis weight; and
   b. an emulsion applied to the carrier, the emulsion comprising:
      (1) from about 5 to about 30% of a continuous, solidified lipid phase comprising a waxy lipid material having a melting point of from about 40° to about 80° C.;
      (2) from about 67 to about 92% of an internal polar phase dispersed in the lipid phase, the internal polar phase comprising at least 75% water; and
      (3) an effective amount of an emulsifier that forms the emulsion when the lipid phase is in a fluid state.

30. The article of claim 29 wherein the aggregate surface area of the plurality of relatively low basis weight regions of the cellulosic fibrous structure comprises at least about 15 percent of the cellulosic fibrous structure's total surface area.

31. The article of claim 30 wherein the aggregate surface area of the plurality of relatively low basis weight regions comprises at least about 20 percent of the cellulosic fibrous structure's total surface area.

32. The article of claim 29 wherein the basis weight of the relatively high basis weight first region is at least about 35% greater than the basis weight of the relatively low basis weight second region.

33. The article of claim 32 wherein the basis weight of the relatively high basis weight first region is at least about 50% greater than the basis weight of the relatively low basis weight second region.

34. An article, which comprises:
   a. a carrier comprising a cellulosic fibrous structure having at least a first region of relatively high basis weight that comprises an essentially continuous network and a second region of a plurality of mutually discrete regions of relatively low basis weight which are circumscribed by the high basis weight first region; and
   b. an emulsion having a continuous external lipid phase and a dispersed polar internal phase applied to the carrier, wherein further the emulsion is prepared by combining at least the following materials:
      (1) from about 2 to about 60% of a waxy lipid material having a melting point of about 30° C. or higher;
      (2) from about 39 to about 97% of a polar material; and
      (3) an effective amount of an emulsifier that forms the emulsion when the waxy lipid is in a fluid state;
      where the weight percent for each of components (1), (2) and (3) is determined from the amount combined relative to the total weight of the emulsion.

35. The article of claim 34 wherein the emulsion comprises from about 5 to about 30% lipid phase and from about 67 to about 92% polar phase.

36. The article of claim 34 wherein the emulsion's internal polar phase comprises at least 75% water.

37. The article of claim 34 wherein the waxy lipid material has a melting point in the range of from about 40° to about 80° C.

38. The article of claim 34 wherein the waxy lipid material is selected from the group consisting of animal waxes, vegetable waxes, mineral waxes, synthetic waxes and mixtures thereof.

39. The article of claim 34 wherein the emulsion further comprises a component selected from the group consisting of perfumes, antimicrobials, detersive surfactants, pharmaceutical actives, deodorants, opacifiers, astringents, insect repellents, bleaches, radical scavengers, chelating agents, thickeners, builders, buffers, stabilizers, bleach activators, soil suspenders, dye transfer agents, brighteners, anti dusting agents, enzymes, dispersants, dye transfer inhibitors, pigments, dyes, and mixtures thereof.

40. The article of claim 34 wherein the aggregate surface area of the plurality of low basis weight regions of the cellulosic fibrous structure is at least about 10% of the cellulosic fibrous structure's total surface area.

41. The article of claim 40 wherein the aggregate surface area of the plurality of low basis weight regions is at least about 20% of the cellulosic fibrous structure's total surface area.

42. The article of claim 34 wherein the basis weight of the high basis weight region is at least about 25% greater than the basis weight of the low basis weight regions.

43. The article of claim 42 wherein the basis weight of the high basis weight region is at least about 35% greater than the basis weight of the low basis weight regions.

44. The article of claim 43 wherein the basis weight of the high basis weight region is at least about 50% greater than the basis weight of the low basis weight regions.

45. The article of claim 34 wherein the carrier further comprises a third region comprising a plurality of mutually discrete regions having a basis weight intermediate to the high basis weight first region and the low basis weight second region, wherein each mutually discrete region having an intermediate basis weight is circumscribed by a discrete low basis weight region.

\* \* \* \* \*